US012807916B2

(12) United States Patent
Malleo et al.

(10) Patent No.: US 12,807,916 B2
(45) Date of Patent: Nov. 24, 2026

(54) SYSTEMS, DEVICES, AND METHODS FOR FLUID CONTROL IN A CELL PROCESSING SYSTEM

(71) Applicant: Cellares Corporation, South San Francisco, CA (US)

(72) Inventors: Daniele Malleo, Menlo Park, CA (US); Bharat Thakkar, Campbell, CA (US); Wilson Wai Toy, San Francisco, CA (US); Matthias Weber, South San Francisco, CA (US); Yiming Xu, San Mateo, CA (US); Joon Mo Yang, Redwood City, CA (US)

(73) Assignee: Cellares Corporation, South San Francisco, CA (US)

( * ) Notice: Subject to any disclaimer, the term of this patent is extended or adjusted under 35 U.S.C. 154(b) by 0 days.

(21) Appl. No.: 18/920,607

(22) Filed: Oct. 18, 2024

(65) Prior Publication Data

US 2025/0129321 A1 Apr. 24, 2025

Related U.S. Application Data

(60) Provisional application No. 63/592,124, filed on Oct. 20, 2023.

(51) Int. Cl.
*C12M 3/00* (2006.01)
*C12M 1/00* (2006.01)
(Continued)

(52) U.S. Cl.
CPC ............ *C12M 29/18* (2013.01); *C12M 23/40* (2013.01); *C12M 27/12* (2013.01); *C12M 29/14* (2013.01); *C12M 41/32* (2013.01); *C12M 41/42* (2013.01)

(58) Field of Classification Search
CPC .............................. C12M 41/42; C12M 29/18
See application file for complete search history.

(56) References Cited

U.S. PATENT DOCUMENTS 3,728,227 A 4/1973 Elson et al.
4,234,023 A 11/1980 Sogi et al.
(Continued)

FOREIGN PATENT DOCUMENTS

CN 104203333 A 12/2014
CN 108660060 A 10/2018
(Continued)

OTHER PUBLICATIONS

ChargePoint (2021). Aseptic split butterfly valve 10-6 sterility assurance, located at https://www.thechargepoint.com/products/aseptic-split-butterfly-valve-10-6-sterility-assurance/, 2 total pages.
(Continued)

*Primary Examiner* — Nathan A Bowers
(74) *Attorney, Agent, or Firm* — Cooley LLP

(57) ABSTRACT

The present disclosure relates to systems, devices, and methods for controlling fluid flow within a cell processing system. In an embodiment, the present disclosure relates to a device having a rotor comprising one or more rollers configured to compress a first fluid conduit, a first lever arm defining a proximal portion and a distal portion, where the first lever arm comprises a first hinge at the proximal portion, and a second hinge in between the proximal portion and the distal portion, a spring coupled to the distal portion, and a second lever arm, where the first and second lever arms are aligned with the rotor and are configured to receive the first fluid conduit.

7 Claims, 13 Drawing Sheets

(51) Int. Cl.
*C12M 1/34* (2006.01)
*C12M 3/04* (2006.01)

(56) References Cited

U.S. PATENT DOCUMENTS 4,673,334 A 6/1987 Allington et al.
4,696,902 A 9/1987 Bisconte
4,839,292 A 6/1989 Cremonese
4,911,833 A 3/1990 Schoendorfer et al.
5,058,619 A 10/1991 Zheng
5,656,491 A 8/1997 Cassani et al.
6,102,678 A * 8/2000 Peclat .................. A61M 5/142 604/93.01
6,267,559 B1 * 7/2001 Mossman ............ F04B 43/082 417/44.1
6,649,419 B1 11/2003 Anderson
7,550,287 B2 6/2009 Hibino et al.
7,745,209 B2 6/2010 Martin et al.
7,816,128 B2 10/2010 Nakashima et al.
8,158,426 B2 4/2012 Wilson et al.
8,158,427 B2 4/2012 Wilson et al.
8,168,432 B2 5/2012 Wilson et al.
8,273,572 B2 9/2012 Martin et al.
8,415,144 B2 4/2013 Wilson et al.
8,440,458 B2 5/2013 Zijlstra et al.
8,470,589 B2 6/2013 Martin et al.
8,492,140 B2 7/2013 Smith et al.
8,546,142 B2 10/2013 Martin et al.
8,671,964 B2 3/2014 Py
8,697,443 B2 4/2014 Wilson et al.
8,727,132 B2 5/2014 Miltenyi et al.
8,809,044 B2 8/2014 Wilson
8,846,399 B2 9/2014 Martin et al.
8,956,860 B2 2/2015 Vera et al.
9,040,290 B2 5/2015 Martin et al.
9,045,721 B2 6/2015 Martin et al.
9,080,149 B2 7/2015 Bosio et al.
9,255,243 B2 2/2016 Wilson et al.
9,279,099 B2 3/2016 Okano et al.
9,290,730 B2 3/2016 Martin et al.
9,410,114 B2 8/2016 Wilson et al.
9,441,192 B2 9/2016 Wilson et al.
9,499,780 B2 11/2016 Smith et al.
9,534,195 B2 1/2017 Smith et al.
9,556,485 B2 1/2017 Lin et al.
9,567,565 B2 2/2017 Vera et al.
9,597,355 B2 3/2017 Magnant
9,625,463 B2 4/2017 Miltenyi et al.
9,701,932 B2 7/2017 Smith et al.
9,726,314 B2 8/2017 Py
9,732,317 B2 8/2017 Wilson
9,783,768 B2 10/2017 Larcher et al.
9,845,451 B2 12/2017 Martin et al.
10,047,342 B2 8/2018 Eibl et al.
10,053,663 B2 8/2018 Kabaha et al.
10,119,970 B2 11/2018 Miltenyi et al.
10,131,876 B2 11/2018 Kaiser et al.
10,253,316 B2 4/2019 Masquelier et al.
10,294,658 B2 5/2019 Scannon et al.
10,323,258 B2 6/2019 Bernate et al.
10,329,559 B1 6/2019 Masquelier et al.
10,385,307 B2 8/2019 Rowley et al.
10,421,959 B1 9/2019 Masquelier et al.
10,508,288 B1 12/2019 Bernate et al.
10,519,437 B1 12/2019 Masquelier et al.
10,533,156 B2 1/2020 Vera et al.
10,584,333 B1 3/2020 Masquelier et al.
10,584,334 B1 3/2020 Masquelier et al.
10,588,994 B2 3/2020 Kawamura et al.
10,620,212 B2 4/2020 Miltenyi et al.
10,689,669 B1 6/2020 Feldman et al.
10,705,090 B2 7/2020 Miltenyi et al.
10,705,091 B2 7/2020 Miltenyi et al.
10,723,986 B2 7/2020 Smith et al.
10,724,043 B2 7/2020 Sixto et al.
10,844,338 B1 11/2020 Smith et al.
11,161,111 B2 11/2021 Kabaha et al.
11,198,845 B2 12/2021 Parietti et al.
11,371,018 B2 6/2022 Shi et al.
11,376,587 B2 7/2022 Thakkar et al.
11,447,745 B2 9/2022 Shi et al.
11,701,654 B2 7/2023 Azersky et al.
11,786,896 B2 10/2023 Thakkar et al.
11,826,756 B2 11/2023 Azersky et al.
11,872,557 B2 1/2024 Biz et al.
12,157,119 B2 12/2024 Gerlinghaus et al.
12,180,453 B2 12/2024 Chang et al.
12,305,156 B2 5/2025 Burkeen et al.
12,337,321 B2 6/2025 Malleo et al.
12,350,664 B2 7/2025 Pesch et al.
12,350,667 B2 7/2025 Azersky et al.
12,350,668 B2 7/2025 Azersky et al.
12,399,193 B2 8/2025 Tian et al.
12,403,468 B2 9/2025 Azersky et al.
12,491,512 B2 12/2025 Biz et al.
12,492,368 B2 12/2025 Carmichael et al.
12,497,587 B2 12/2025 Grout et al.
D1,109,621 S 1/2026 Cesarek et al.
12,551,887 B2 2/2026 Biz et al.
12,559,710 B2 2/2026 Azersky et al.
12,570,948 B2 3/2026 Thakkar et al.
2003/0030272 A1 2/2003 Johnson et al.
2005/0053502 A1 3/2005 Souza
2005/0260743 A1 11/2005 Drake et al.
2006/0194193 A1 8/2006 Tsuruta et al.
2006/0257999 A1 11/2006 Chang et al.
2007/0185472 A1 8/2007 Baumfalk et al.
2008/0057568 A1 3/2008 Kan et al.
2008/0176318 A1 7/2008 Wilson et al.
2008/0254533 A1 10/2008 Antwiler
2009/0042281 A1 2/2009 Chang et al.
2009/0247417 A1 10/2009 Haas et al.
2010/0172045 A1 7/2010 Goodman et al.
2010/0301071 A1 * 12/2010 Alstad ................. F04B 43/1269 417/477.3
2011/0003380 A1 1/2011 Miltenyi et al.
2012/0138156 A1 6/2012 Hofman et al.
2012/0148415 A1 6/2012 Brueckner
2013/0115617 A1 5/2013 Wilson
2013/0189120 A1 * 7/2013 Nelson ................ F04B 43/1261 417/474
2014/0309795 A1 10/2014 Norton et al.
2015/0158907 A1 * 6/2015 Zhou ...................... C12M 41/00 530/399
2015/0307829 A1 10/2015 Dedry et al.
2016/0208216 A1 7/2016 Vera et al.
2016/0303563 A1 10/2016 Granier et al.
2016/0320381 A1 11/2016 Holmes et al.
2016/0320422 A1 11/2016 Fritchie et al.
2017/0014149 A1 1/2017 Nakayashiki et al.
2017/0058257 A1 3/2017 Levner et al.
2017/0058527 A1 3/2017 Williams et al.
2017/0239420 A1 * 8/2017 Wells ................. A61B 17/3468
2017/0248697 A1 8/2017 Lo
2017/0307502 A1 10/2017 Mason et al.
2017/0313977 A1 11/2017 Wilson
2017/0321226 A1 11/2017 Gill et al.
2017/0362554 A1 12/2017 Martin et al.
2018/0031592 A1 2/2018 Dority
2018/0051243 A1 2/2018 Hogan et al.
2018/0078935 A1 3/2018 Hung et al.
2018/0185849 A1 7/2018 Kaplan et al.
2018/0196918 A1 7/2018 Sadowski et al.
2019/0002874 A1 1/2019 Belgrader et al.
2019/0212233 A1 7/2019 Jovanovich et al.
2019/0275519 A1 9/2019 Castillo et al.
2019/0292510 A1 9/2019 Tandon et al.
2019/0316120 A1 10/2019 Masquelier et al.
2020/0009557 A1 1/2020 Frigard et al.
2020/0025782 A1 1/2020 Ahlfors
2020/0095550 A1 3/2020 Vera et al.
2020/0132534 A1 4/2020 Luedemann
2020/0159198 A1 5/2020 Kapre et al.
2020/0283713 A1 9/2020 Ball et al.

(56) References Cited

U.S. PATENT DOCUMENTS

2020/0292552 A1 9/2020 Miltenyi et al.
2020/0353004 A1 11/2020 Nowak et al.
2020/0368411 A1 11/2020 Camisani et al.
2020/0406221 A1 12/2020 Dabrowski et al.
2021/0032583 A1 2/2021 Smith et al.
2021/0035655 A1 2/2021 Tanouchi et al.
2021/0047668 A1 2/2021 Dabrowski et al.
2021/0079344 A1 3/2021 Bosio et al.
2021/0147807 A1 5/2021 Lickert et al.
2021/0244255 A1* 8/2021 Haegermarck ..... A47L 15/4291
2021/0253997 A1 8/2021 Wilson
2021/0269755 A1 9/2021 Smith et al.
2021/0283565 A1 9/2021 Gerlinghaus et al.
2021/0283606 A1 9/2021 Thakkar et al.
2021/0301239 A1 9/2021 Natsume et al.
2021/0324318 A1 10/2021 Parietti et al.
2021/0354104 A1 11/2021 Pesch et al.
2021/0403847 A1 12/2021 Takayama et al.
2022/0002652 A1 1/2022 Patrick et al.
2022/0127558 A1 4/2022 Sowwan et al.
2022/0143610 A1 5/2022 Biz et al.
2022/0150650 A1 5/2022 Rucker
2022/0163438 A1 5/2022 Klas et al.
2022/0282199 A1 9/2022 Vann
2022/0284574 A1 9/2022 Wagner et al.
2022/0325219 A1 10/2022 Parietti et al.
2022/0347683 A1 11/2022 Thakkar et al.
2023/0044320 A1 2/2023 Chalony et al.
2023/0149922 A1 5/2023 Thakkar et al.
2023/0159917 A1 5/2023 Handique et al.
2023/0321650 A1 10/2023 Azersky et al.
2023/0415154 A1 12/2023 Pesch et al.
2023/0415155 A1 12/2023 Biz et al.
2024/0018955 A1* 1/2024 Hannah ............... F04B 43/1253
2024/0165613 A1 5/2024 Azersky et al.
2024/0167466 A1* 5/2024 Paraluppi ............ F04B 43/1253
2024/0240764 A1* 7/2024 Gabrielli ................. F04D 13/06
2024/0254426 A1 8/2024 Elpel et al.
2024/0255537 A1 8/2024 Malleo et al.
2024/0279585 A1 8/2024 Griffin et al.
2024/0279588 A1 8/2024 Malleo et al.
2024/0318116 A1 9/2024 Chang et al.
2024/0326043 A1 10/2024 Gerlinghaus et al.
2024/0369586 A1 11/2024 Tian et al.
2024/0377420 A1 11/2024 Cesarek
2024/0390897 A1 11/2024 Azersky et al.
2024/0390898 A1 11/2024 Azersky et al.
2024/0399365 A1 12/2024 Biz et al.
2024/0402206 A1 12/2024 Boppart et al.
2024/0426292 A1* 12/2024 Barrett .................... F04B 51/00
2025/0002837 A1 1/2025 Bharat
2025/0059492 A1 2/2025 Beban et al.
2025/0065331 A1 2/2025 Malleo et al.
2025/0066708 A1 2/2025 Burkeen et al.
2025/0066709 A1 2/2025 Grout et al.
2025/0207076 A1 6/2025 Marchiando et al.
2025/0236832 A1 7/2025 Chang et al.
2025/0283026 A1 9/2025 Carmichael et al.
2025/0304904 A1 10/2025 Azersky et al.
2025/0360504 A1 11/2025 Azersky et al.
2025/0367660 A1 12/2025 Biz et al.
2025/0368943 A1 12/2025 Burkeen et al.
2025/0375767 A1 12/2025 Malleo et al.
2026/0029422 A1 1/2026 Malleo et al.
2026/0056220 A1 2/2026 Tian et al.
2026/0139217 A1 5/2026 Grout et al.

FOREIGN PATENT DOCUMENTS

DE 69700070 T2 5/1999
EP 0246912 A2 11/1987
EP 0991389 A1 4/2000
EP 0824380 B1 1/2002
EP 1185612 B1 8/2004
EP 3134512 B1 1/2019
EP 2809449 B1 10/2019
EP 3359294 B1 5/2020
EP 3928867 A1 12/2021
GB 2268187 A 1/1994
JP 2007325586 A 12/2007
JP 6264698 B2 1/2018
KR 20130018286 A 2/2013
WO WO-1986000231 A1 1/1986
WO WO-2006102416 A2 9/2006
WO WO-2006112870 A1 10/2006
WO WO-2006118282 A1 11/2006
WO WO-2007139742 A1 12/2007
WO WO-2009072003 A2 6/2009
WO WO-2017041051 A1 3/2017
WO WO-2017123663 A1 7/2017
WO WO-2018015561 A1 1/2018
WO WO-2018102471 A1 6/2018
WO WO-2019232504 A2 12/2019
WO WO-2020009700 A1 1/2020
WO WO-2020014264 A1 1/2020
WO WO-2021168368 A1 8/2021
WO WO-2021183687 A2 9/2021
WO WO-2021212124 A1 10/2021
WO WO-2023055543 A1 4/2023
WO WO-2024044161 A1 2/2024
WO WO-2024112702 A1 5/2024
WO WO-2024206703 A1 10/2024
WO WO-2025007051 A2 1/2025
WO WO-2025038974 A1 2/2025
WO WO-2025041046 A1 2/2025
WO WO-2025202944 A2 10/2025
WO WO-2026003813 A2 1/2026
WO WO-2026083353 A1 4/2026

OTHER PUBLICATIONS

CPC (2014). "6 traits of non-spill: How quick disconnect couplings evolved for low-pressure fluid handling," White Paper 8004, 4 total pages.
CPC (2014). "How single-use connections advance aseptic processing: Increased process flexibility and reliability, reduced costs," White Paper 7004, 6 total pages.
CPC (2018). Comparison Guide: Tube Welders and Aseptic Connectors, Technical Guide 7009, 3 total pages.
EMD Millipore (2015). "Lynx® S2S Connector—Low temperature compatibility (-80"C)," 4 total pages.
Final Office Action for U.S. Appl. No. 17/331,554 mailed Aug. 29, 2024, 18 pages.
Final Office Action for U.S. Appl. No. 18/799,963 mailed Jan. 30, 2025, 10 pages.
Final Office Action mailed on Apr. 28, 2022, for U.S. Appl. No. 17/198,134, filed Mar. 10, 2021, 11 pages.
Final Office Action mailed on Apr. 28, 2022, for U.S. Appl. No. 17/331,554, filed May 26, 2021, 16 pages.
Final Office Action mailed on Jul. 31, 2023, for U.S. Appl. No. 17/331,554, filed May 26, 2021, 19 pages.
Final Office Action mailed on Mar. 31, 2023, for U.S. Appl. No. 17/579,478, filed Jan. 19, 2022, 8 pages.
Garcia et al., "Microfluidic Screening of Electric Fields for Electroporation" Sci Rep. Feb. 19, 2016; 6:21238. pp. 1-11.
Genetic Engineering & Biotechnology News (2006). "Thermal welding for sterile connections," located at https://www.genengnews.com/magazine/47/thermal-welding-for-sterile-connections/, 5 total pages.
International Search Report and Written Opinion for PCT Application No. PCT/IB2024/058105 mailed Dec. 16, 2024, 12 pages.
International Search Report and Written Opinion for PCT Application No. PCT/US2024/022079 mailed Sep. 12, 2024, 25 pages.
International Search Report and Written Opinion for PCT Application No. PCT/US2024/042795 mailed Dec. 16, 2024, 11 pages.
International Search Report mailed on Oct. 13, 2021, for PCT Application No. PCT/US2021/021773, filed on Mar. 10, 2021, 13 pages.
Invitation to Pay Additional Fees for International Application No. PCT/US2024/022079 dated Jul. 17, 2024, 19 pages.

(56) References Cited

OTHER PUBLICATIONS

Jain, S. et al. (2011). "The complete automation of cell culture: improvements for high-throughput and high-content screening," J. Biomol. Screen 16:932-939.
Kato, R. et al. (2010). "A Compact, Automated Cell Culture System for Clinical Scale Cell Expansion from Primary Tissues," Tissue Engineering: Part C 16:947-956.
Kempner, M.E. and Felder, R.A., "A review of cell culture automation". JALA: Journal of the Association for Laboratory Automation (Apr. 2002); 7(2): 56-62.
Kino-Oka, M. et al. (2005). "Bioreactor Design for Successive Culture of Anchorage-Dependent Cells Operated in an Automated Manner," Tissue Engineering 11:535-545.
Knoll, A. et al. (2004). "Flexible automation of cell culture and tissue engineering tasks," Biotechnol. Prog. 20:1825-1835.
Lutkemeyer, D. et al. (2000). "First steps in robot automation of sampling and sample management during cultivation of mammalian cells in pilot scale," Biotechnol. Prog. 16:822-828.
MEDInstill (2021). INTACT™ Connectors, located at https://www.medinstill.com/intactconnectors.php, 1 total page.
Millipore® (2020). "Technical Brief—Choosing the right sterile connector based on design and sterility test results," 4 total pages.
Millipore Sigma (2020). "Lynx® CDR Connectors," Datasheet, 4 total pages.
Millipore Sigma (2021). Lynx® CDR Connectors, located at https://www.emdmillipore.com/US/en/product/Lynx-CDR-Connectors,MM_NF-C188801, 2 total pages.
Non-Final Office Action for U.S. Appl. No. 18/244,051 mailed Oct. 9, 2024, 10 pages.
Non-Final Office Action for U.S. Appl. No. 18/759,602 mailed Nov. 8, 2024, 10 pages.
Non-Final Office Action for U.S. Appl. No. 18/792,358 mailed on Nov. 6, 2024,5 pages.
Non-Final Office Action for U.S. Appl. No. 18/799,963 mailed Sep. 30, 2024,9 pages.
Non-Final Office Action mailed on Apr. 24, 2024, for U.S. Appl. No. 17/331,554, filed May 26, 2021, 17 pages.
Non-Final Office Action mailed on Dec. 22, 2022, for U.S. Appl. No. 17/579,478, filed Jan. 19, 2022, 8 pages.
Non-Final Office Action mailed on Dec. 3, 2021, for U.S. Appl. No. 17/331,556, filed May 26, 2021, 9 pages.
Non-Final Office Action mailed on Feb. 3, 2022, for U.S. Appl. No. 17/198,134, filed on Mar. 10, 2021, 5 pages.
Non-Final Office Action mailed on Jun. 26, 2023, for U.S. Appl. No. 17/198,134, filed Mar. 10, 2021, 15 pages.
Non-Final Office Action mailed on Mar. 16, 2023, for U.S. Appl. No. 17/331,554, filed May 26, 2021, 16 pages.
Non-Final Office Action mailed on Oct. 28, 2021, for U.S. Appl. No. 17/331,554, filed May 26, 2021, 11 pages.
Non-Final Office Action mailed on Oct. 6, 2021, for U.S. Appl. No. 17/198,134, filed on Mar. 10, 2021, 7 pages.
Non-Final Office Action mailed on Sep. 13, 2023, for U.S. Appl. No. 18/141,329, filed Apr. 28, 2023, 7 pages.
Notice of Allowance for U.S. Appl. No. 18/792,360 mailed on Jan. 29, 2025, 9 pages.
Notice of Allowance for U.S. Appl. No. 18/810,388 mailed Jan. 21, 2025, 8 pages.
Notice of Allowance for U.S. Appl. No. 18/810,388 mailed on Oct. 9, 2024, 9 pages.
Notice of Allowance mailed on Apr. 11, 2024, for U.S. Appl. No. 17/198,134, filed Mar. 10, 2021, 9 pages.
Notice of Allowance mailed on Jul. 18, 2023, for U.S. Appl. No. 17/849,422, filed Jun. 24, 2022, 8 pages.
Notice of Allowance mailed on Jul. 25, 2023, for U.S. Appl. No. 17/579,478, filed Jan. 19, 2022, 8 pages.
Notice of Allowance mailed on Jun. 8, 2023, for U.S. Appl. No. 17/849,422, filed Jun. 24, 2022, 8 pages.
Notice of Allowance mailed on Mar. 1, 2022, for U.S. Appl. No. 17/331,556, filed May 26, 2021, 8 pages.
Notice of Allowance mailed on Mar. 22, 2023, for U.S. Appl. No. 17/992,784, filed Nov. 22, 2022, 8 pages.
Notice of Allowance mailed on Oct. 4, 2023, for U.S. Appl. No. 18/141,329, filed Apr. 28, 2023, 8 pages.
Pharma Japan, "Astellas Set to Cut Development Time with Cell Culture Robot, Eyes 4 Billion Yen Profit per Product" Aug. 9, 2023, 3 pages.
Qu, B. et al., "Droplet Electroporation in Microfluidics for Efficient Cell Transformation with or without Cell Wall Removal," Lab Chip (2012) 12:4483-4488.
Saint Gobain (2017). "Pure-Fit® SC—Secure aseptic connections," Brochure, 5 total pages.
Sartorius Stedim Biotech (2011). "Opta® SFT," 4 total pages.
Schwartz C., "Optimizing Cell Separation with Beckman Coulter's Centrifugal Elutriation System," Beckmann Coulter Life Sciences (2014) 6 total pages.
SeriesLock™ (2021). Features and Specifications, located at https://serieslock.com/, 5 total pages.
Shi, Y. et al. (1992). "Performance of Mammalian Cell Culture Bioreactor with a New Impeller Design," Biotechnology and Bioengineering 40:260-270.
STERIS (2018). "A compilation of material compatibilities with vaporized hydrogen peroxide," 2 total pages.
STERIS (2018). "Sterility assurance levels (SALS): Irradiation," 3 total pages.
STERIS (2020). "Overview of sterilization technology comparison," 1 total page.
Strahlendorf, K.A. et al. (2009). "Bio Pharm International—A review of sterile connectors," vol. 2009 Supplement, Issue 8, located at https://www.biopharminternational.com/view/review-sterile-connectors, 9 total pages.
U.S. Appl. No. 18/807,699, filed Aug. 16, 2024, by Beban et al.
U.S. Appl. No. 29/898,923, filed Aug. 2, 2023, by Gerlinghaus et al.
Written Opinion of the International Searching Authority mailed on Oct. 13, 2021, for PCT Application No. PCT/US2021/021773, filed on Mar. 10, 2021, 20 pages.
Final Office Action for U.S. Appl. No. 18/244,051 mailed Apr. 4, 2025, 11 pages.
Final Office Action for U.S. Appl. No. 18/759,602 mailed on May 28, 2025, 12 pages.
Non-Final Office Action for U.S. Appl. No. 18/759,602 mailed Feb. 20, 2025, 15 pages.
Non-Final Office Action for U.S. Appl. No. 18/807,699 mailed Apr. 29, 2025, 19 pages.
Notice of Allowance for U.S. Appl. No. 17/331,554 mailed Apr. 10, 2025, 6 pages.
Notice of Allowance for U.S. Appl. No. 17/331,554 mailed Mar. 5, 2025, 8 pages.
Notice of Allowance for U.S. Appl. No. 18/487,884 mailed Feb. 26, 2025, 8 pages.
Notice of Allowance for U.S. Appl. No. 18/487,884 mailed on Apr. 3, 2025, 8 pages.
Notice of Allowance for U.S. Appl. No. 18/792,358 mailed on Mar. 3, 2025, 8 pages.
Notice of Allowance for U.S. Appl. No. 18/792,360 mailed Mar. 4, 2025, 9 pages.
Notice of Allowance for U.S. Appl. No. 18/810,388 mailed Apr. 30, 2025, 5 pages.
U.S. Appl. No. 18/988,628, filed Dec. 19, 2024, by Marchiando et al.
U.S. Appl. No. 18/807,699, Final Office Action mailed Aug. 20, 2025; Inventor Beban, Marc et al.; 22 pages.
PCT Application No. PCT/US2024/036245, International Search Report and Written Opinion mailed Jun. 11, 2025; Applicant Cellares Corporation; 13 pages.
U.S. Appl. No. 19/091,700, Non-Final Office Action mailed Jul. 7, 2025; Inventor Azersky, Vladmir et al.; 13 pages.
U.S. Appl. No. 18/244,051, Notice of Allowance mailed Oct. 15, 2025; Inventor Biz, Tony et al.; 5 pages.
U.S. Appl. No. 18/799,963, Notice of Allowance mailed Jul. 1, 2025; Inventor Biz, Tony et al.; 7 pages.
U.S. Appl. No. 19/075,709, Notice of Allowance mailed Jul. 29, 2025; Inventor Carmichael, Stephen et al.; 10 pages.

(56) References Cited

OTHER PUBLICATIONS

U.S. Appl. No. 19/091,700, Notice of Allowance mailed Oct. 22, 2025; Inventor Azersky, Vladmir et al.; 9 pages.
Shabalina et al., "ARTag, AprilTag and CALTag Fiducial Systems Comparison in a Presence of Partial Rotation: Manual and Automated Approaches" in ICINCO (2017) LNEE 495:536-558.
PCT Application No. PCT/IB2025/053219, International Search Report and Written Opinion mailed Jan. 23, 2026, Applicant Cellares Corporation; 17 pages.
PCT Application No. PCT/IB2025/053219, Invitation to Pay Additional Fees mailed Nov. 25, 2025; Applicant Cellares Corporation; 13 pages.
PCT Application No. PCT/IB2025/056591, Invitation to Pay Additional Fees mailed May 20, 2026, Applicant Cellares Corporation.; 16 pages.
PCT Application No. PCT/IB2025/060633, International Search Report and Written Opinion mailed Dec. 15, 2025, Applicant Cellares Corporation.; 13 pages.
U.S. Appl. No. 18/244,047, Non-Final Office Action mailed May 6, 2026; Inventor Pesch, Brian Alexander et al.; 7 pages.
U.S. Appl. No. 18/759,602, Notice of Allowance mailed Nov. 10, 2025; Inventor Thakkar, Bharat S. et al.; 9 pages.
U.S. Appl. No. 19/295,488, Non-Final Office Action mailed Dec. 18, 2025; Inventor Biz, Tony et al.; 9 pages.
U.S. Appl. No. 19/295,488, Notice of Allowance mailed Apr. 21, 2026; Inventor Biz, Tony et al.; 7 pages.
U.S. Appl. No. 19/371,847, filed Oct. 28, 2025; Inventor Carmichael, Stephen.
U.S. Appl. No. 19/392,013, filed Nov. 17, 2025; Inventor Grout, Wayne E et al.
U.S. Appl. No. 19/534,547, filed Feb. 9, 2026; Inventor Thakkar, Bharat S et al.

* cited by examiner

SYSTEMS, DEVICES, AND METHODS FOR FLUID CONTROL IN A CELL PROCESSING SYSTEM

CROSS REFERENCE TO RELATED APPLICATIONS

This application claims priority to U.S. Provisional Patent Application No. 63/592,124 filed Oct. 20, 2023, the content of which is incorporated herein by reference in its entirety for all purposes.

TECHNICAL FIELD

The present disclosure relates to systems, devices, and methods for pumping fluid, for example, pumping fluid within systems and devices useful in cell processing.

BACKGROUND

Cell therapies involve collecting cells from an individual, processing the cells, and utilizing the processed cells to achieve a clinical response in the same or a different individual. Cell processing is a complex workflow that involves multiple steps, where each step typically requires a separate cell processing device and/or system to accomplish the specific step. Fluids, such as cellular material, may need to be transferred between different cell processing devices in order to achieve the final cell output. Improvements to cell processing systems have been made where multiple cell processing devices have been replaced by multiple modules within a single cartridge. However, even in these improved systems, fluids and cellular material must be transferred between the modules in order to perform distinct cell processing steps. Therefore, each module is typically fluidically connected to a fluid source by a fluid conduit. A fluid pump is typically used to pump the fluid through the fluid conduit. Each module may require a specific flow rate of fluid, which may be different than the flow rates required for other modules. Fluid pumps directing flow to these modules may cause pulses in the fluid flow, which in turn may disrupt the cell processing steps of a given module. Furthermore, some fluid pumps are comprised of multiple parts and these parts can become misaligned during use, such that the fluid pump may not adequately pump fluid. Other issues may be present as well, which can require manual intervention to rectify. Accordingly, additional systems and methods for pumping fluids in a cell processing system are desirable.

SUMMARY

The present disclosure relates generally to systems, devices, and methods for pumping fluid, for example, during cell processing. In general, a device for pumping fluid may include a rotor, a first lever arm, a second lever arm, and a spring. The rotor may include one or more rollers configured to compress a fluid conduit. In some variations, the one or more rollers may comprise at least three rollers, at least five rollers, or between six and ten rollers.

The first lever arm may define a proximal portion and a distal portion and may include a first hinge at the proximal portion and a second hinge in between the proximal portion and the distal portion. In some variations, the second hinge may be positioned equidistantly between the proximal portion and the distal portion. The second lever arm may be coupled to the second hinge. The second lever arm may be configured to rotate relative to the first lever arm. The first and second lever arms may be aligned with the rotor and may be configured to receive the fluid conduit. The spring may be coupled to the distal portion. The spring may comprise a spring force between about 20 N and about 30 N.

The device may further include a motor operatively coupled to the rotor. The motor may be configured to rotate the rotor up to about 20 rotations per minute or between about 10 rotations per minute and about 30 rotations per minute. The device may further include a controller for controlling the rotor. The device may further include one or more sensors operatively coupled to the rotor. In some variations, the device may further include a second rotor having one or more rollers configured to compress a second fluid conduit.

In some variations, a device for pumping fluid may include a closed-loop fluid pump having a fluid conduit, a rotor having one or more rollers configured to compress the fluid conduit upon rotation of the rotor, a first lever arm and a second lever arm, a spring coupled to at least one of the first and second lever arms, a flow sensor configured to measure the flow rate through the fluid conduit, and a controller configured to modify the rotation of the rotor based on the flow rate measurement. The flow rate may be between about 1 mL/min and about 15 mL/min or at least about 5 mL/min. The flow rate may be measured during a first rotation of the rotor and estimated during a second rotation of the rotor.

Methods of controlling fluid flow are also described herein. A method of controlling fluid flow may include providing fluid to a first fluid conduit of a pump assembly, pumping the fluid through the first fluid conduit via rotation of the rotor, measuring one or more of a torque value and a rotor position value, and modifying the rotation of the rotor based on the one or more measurements to modify fluid flow through the first fluid conduit. Modifying the rotation of the rotor may be performed in a closed loop or an open loop. The pump assembly may further include a lever arm and a rotor operatively coupled to a pump motor. The rotor may include one or more rollers configured to compress the first fluid conduit. The rotor may rotate at a rate between about 1 rpm and about 20 rpm.

The methods may further include measuring one or more of a motor power value, a motor current value, a sensor distance value, and a pressure value. An empirical model may be used to estimate a flow rate of the fluid flow through the first fluid conduit. In some variations, the method may further include providing fluid to a second fluid conduit of the pump assembly. A non-zero flow rate may be maintained through one or more of the first fluid conduit and the second fluid conduit.

Additional embodiments, features, and advantages of the invention will be apparent from the following detailed description and through practice of the invention.

DETAILED DESCRIPTION

Figure 1A:
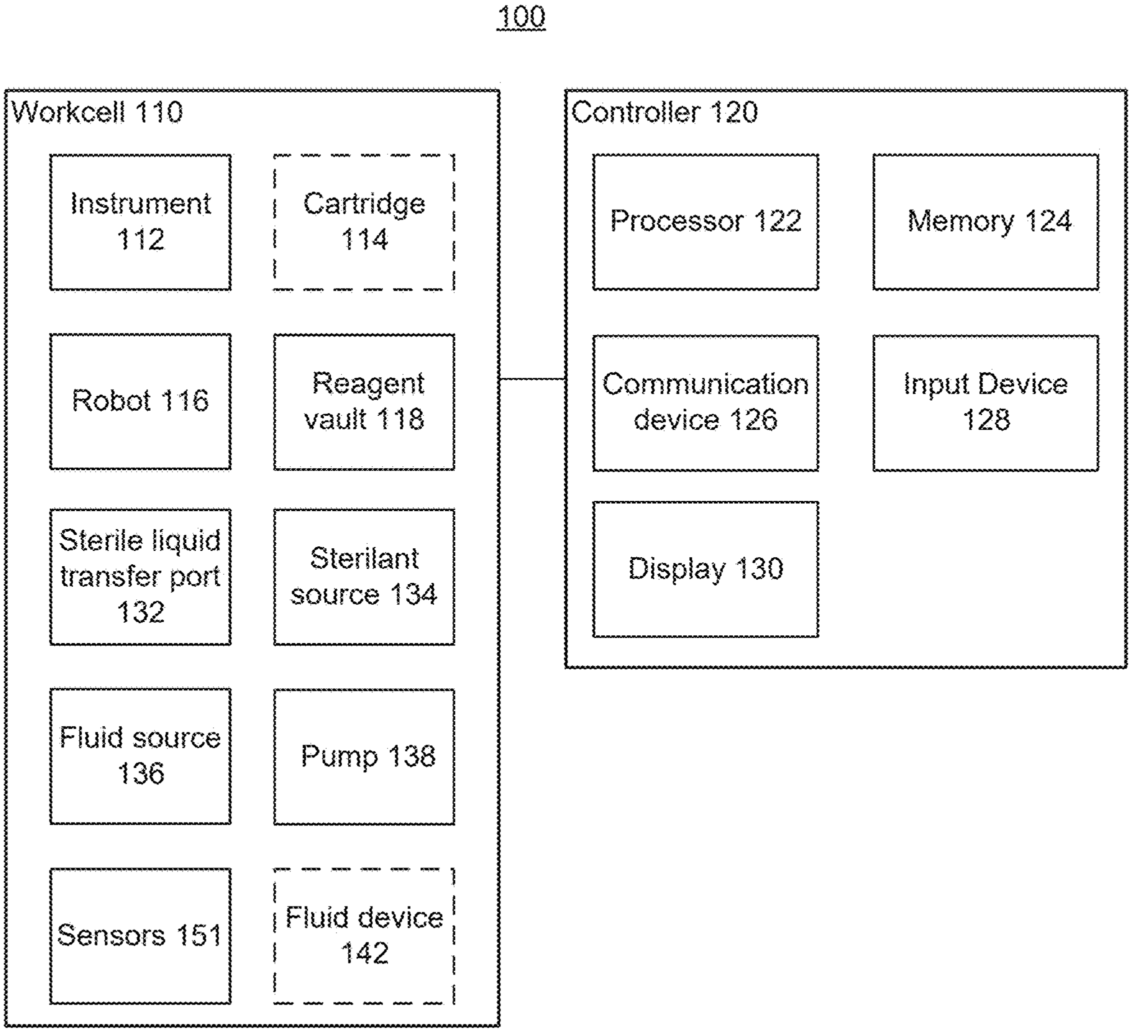
FIG. 1A is a block diagram of an illustrative variation of a cell processing system.

Disclosed herein are devices, systems, and methods for controlling fluid flow, for example, controlling fluid flow to and from cell processing modules of one or more cell processing cartridges to facilitate processing cells. Multiple cell processes, or cell processing steps, may be performed on cells within a cell processing system (e.g., workcell). The cell processing steps may each require one or more fluids (e.g., a cell suspension, a media, a buffer, a reagent). The one or more fluids may be provided to one or more modules of a cartridge of the workcell according to a pre-defined workflow. Accordingly, one or more fluids may be transferred by a pump module of the cartridge, such that the pump module (e.g., fluid pumping device) may control quantity, flow rate, and/or timing of any fluid flowing therethrough. That is, the pump module may be connected to the one or more modules of the cartridge by one or more fluid conduits (e.g., tubes or channels). For example, the pump module may be fluidically connected to one or more of an elutriation module, a fluidic manifold, an electroporation module, a spinoculation module, and a cell sorting module. The pump module may comprise one or more pumps configured to control fluid flow through one or more fluid conduits.

The pump module may be configured to maintain a consistent flow rate of fluid pumped therethrough. In this way, the pump module may avoid pulses in fluid transferred to one or more other modules, which may advantageously avoid interrupting cell processing steps that may require a specific flow rate and/or a specific total volume. For example, if one or more pulses were to occur, a volume greater than the desired total volume may be delivered by the pump module. Furthermore, the pump module may be configured to accommodate vibrations caused by any cell processing step described herein, such that fluid may consistently flow through the pump module. Similarly, the pump module may be configured to maintain alignment between the pumping device and the fluid conduit through which fluid may flow. Maintaining proper alignment may provide for consistent and/or predictable contact between the rotor and the fluid conduit, which may advantageously facilitate a consistent flow rate which, in turn, may be used to provide a specific total volume of fluid.

The pump modules described herein may be configured to pump fluid to and/or from one or more modules of a cartridge of a cell processing workcell such that risk of contamination of the fluid may be minimized. For example, the pump modules may be configured to engage an external surface of a fluid conduit, such that any fluid flowing through the fluid conduit avoid contact with any other components. The pump modules may pump fluid by intermittently compressing a fluid conduit. For example, a pump module may comprise a peristaltic pump having a rotor with one or more rollers. The rotor may rotate such that the one or more rollers translate along a surface of the fluid conduit. The fluid conduit may be compressed by the one or more rollers as the one or more rollers translates along the surface of the fluid conduit. The compression creates a volume of low pressure (e.g., a vacuum) at the point of compression (e.g., occlusion), such that fluid may move from a volume of higher pressure to the volume of low pressure. Accordingly, translating the compressive force along the fluid conduit causes fluid to move through the fluid conduit and out of the pump module.

The pump modules described herein may provide fluid to one or more modules at a consistent flow rate, despite the intermittent compression of one or more fluid conduits. For example, in some predicate designs, the intermittent compression of the fluid conduit may result in pulses in the fluid flow, such that fluid may not be pumped to a destination at a consistent flow rate. However, the pump modules described herein may eliminate such pulses and thus may facilitate a consistent flow rate. For example, a rate of rotation of the rotor may be variable such that the flow rate may be maintained at a consistent value. In particular, a volumetric liquid flow rate may be proportional to a cross-sectional area of the fluid conduit and the rate of rotation of the rotor. Accordingly, a decrease in the rate of rotation when the cross-sectional area is large and an increase in the rate of rotation when the cross-sectional area is small may yield a comparatively smoother flow rate. Furthermore, flow through more than one fluid conduits may be combined such that any remaining inconsistencies in a flow rate of an individual fluid conduit may be mitigated by the flow rate of fluid from a different fluid conduit (e.g., destructive interference).

Accordingly, the pump modules described herein may enable an adjustable number of modules to receive fluid at a required flow rate. In turn, the adjustable of the modules may facilitate a flexible workflow, such that the workflow may be modified to increase the total throughput of cellular byproducts for use in cell therapies. Accordingly, the pump modules described herein may be useful in performing high-throughput cell processing in cell processing systems.

I. Cell Processing System

The cell processing systems described herein may be configured to perform one or more cell processing steps in a workcell. The workcell may comprise a closed, automated environment, which may be configured to maintain a sterile environment. The workcell may receive a cartridge and perform one or more cell processing steps on cells in a cell solution (e.g., cell suspension) contained within the cartridge. For example, the cell processing system may comprise a workcell comprising a plurality of instruments that may each be configured to independently perform one or more cell processing steps to the cells and/or cell solution, and a robot capable of moving the cartridge within the workcell (e.g., between one or more bays). The robot and/or instruments may be configured to automatically operate such that operator assistance may not be required at any point during the workflow. For example, the robot may receive the cartridge and move the cartridge between locations (e.g., instruments, bays, storage vaults, feedthroughs) within the workcell according to a pre-programmed workflow, where each location may be associated with one or more cell processing steps. After performing one or more cell processing steps of the pre-programmed workflow, the workcell may be configured to transfer the cartridge out of the workcell (e.g., via the robot). Additionally or alternatively, at least a portion of the cell solution may be transferred (e.g., via a fluid device or a fluidic manifold) to a second cartridge.

The cell solution (e.g., cell suspension) described herein may contain cells that may be processed for subsequent use in cell therapies. The cell solution may comprise cells (e.g., allogeneic cells) in a fluid, such as a media (e.g., cell culture media). The cell solution may contain cells from the same or different donors. Cells from the same donor may be split between one or more cartridges, such that separate cell processing steps may be performed on each of the cartridges and increase the overall throughput of the cell processing system described herein. The cell solution may be transferred to the cartridge prior to loading the cartridge into the workcell, such as by operating personnel. In some variations, the cartridge may be empty when loaded into the workcell such that the workcell may transfer a cell solution to the cartridge. In some variations, the cells from two or more cartridges may be combined according to a predetermined ratio, which may correspond to an intended therapeutic treatment for a patient.

An illustrative cell processing system utilizing the pump modules disclosed herein is shown in FIG. 1A. Shown there is a block diagram of a cell processing system 100 comprising a workcell 110 and controller 120. The workcell 110 may comprise one or more of an instrument 112, a robot 116 (e.g., robotic arm), a reagent vault 118, a sterile liquid transfer port 132, a sterilant source 129, a fluid source 136, a pump 138, and a sensor(s) 151. A cartridge 114 and a fluid device 142, which may be provided outside of the workcell 110 and used within the workcell 110, are illustrated in dashed lines. In some variations, the fluid device 142 may be a sterile liquid transfer device (SLTD). However, it should be appreciated that the fluid device 142 may be configured to transfer any fluid (which includes liquids), whether sterile or not. The controller 120 may comprise one or more of a processor 122, a memory 124, a communication device 126, an input device 128, and a display 130.

The workcell 110 may comprise a fully, or at least partially, enclosed housing inside which one or more cell processing steps may be performed in a fully, or at least partially, automated process. The cartridge 114 may be moved using the robot 116 to reduce manual labor in the cell processing steps, and fluid transfers into and out of the cartridge 114 may also be performed in a fully or partially automated process. For example, one or more fluids may be stored in a fluid device 142, such that the one or more fluids may be transferred to the cartridge 114 and/or removed from the cartridge 114 via the fluid device 142. In some variations, the fluid device 114 may be moved within the system 100 by the robot 116. Accordingly, the workcell 110 advantageously enables the transfer of fluids using the pump modules described herein in an automated and metered manner for automating cell therapy manufacturing.

The workcell 110 may facilitate fluid transfers and/or cartridge transfers. For example, in some variations, the robot 116 may be configured to move more than one cartridge 114 between different bays to perform a predetermined sequence of cell processing steps (e.g., workflow). In this way, multiple cartridges 114 may be processed in parallel, as different steps of the cell processing workflow may be performed at the same time on different cartridges. In another example, a sterile liquid transfer port 132 may be coupled between two or more cartridges 114 to transfer a cell product and/or other fluid between the cartridges 114. Furthermore, the sterile liquid transfer port 132 may be coupled between any set of fluid-carrying components of the system 100 (e.g., cartridge 114, reagent vault 118, fluid source 136, fluid device 142, etc.). For example, a first sterile liquid transfer port may be coupled between a first cartridge and a corresponding sterile liquid transfer port of a fluid device.

Other suitable cell processing systems and aspects thereof are provided in, e.g., U.S. patent application Ser. No. 17/198,134, published as U.S. Patent Publication No. 2021/0283565, U.S. Patent Application No. 63/470,381, U.S. Patent Application No. 63/524,596, U.S. Patent Application No. 63/520,313, U.S. Patent Application No. 63/520,312, U.S. Patent Application No. 63/537,730, U.S. Patent Application No. 63/520,858, U.S. Patent Application No. 63/520,859, and U.S. Patent Application No. 63/520,861, each of which is incorporated in their entirety by reference herein.

A. Cartridge

The cell processing systems for use with the pump modules described herein may comprise one or more cartridges having one or more modules configured to interface with, or releasably couple to, one or more instruments within the workcell. Some or all of the modules may be integrated in a fixed configuration within the cartridge, though they need not be. Indeed, one or more of the modules may be configurable or moveable within the cartridge, permitting various formats of cartridges to be assembled. For example, the cartridge may be a single, closed unit with fixed components for each module, or the cartridge may contain configurable modules coupled by configurable fluidic, mechanical, optical, and electrical connections. In some variations, one or more sub-cartridges, each containing a set of modules, may be used to perform various cell processing workflows. The modules may each be provided in a distinct housing or may be integrated into a cartridge or sub-cartridge with other modules. The disclosure generally shows modules as distinct groups of components for the sake of simplicity, but it should be noted that these modules may be arranged in any suitable configuration. For example, the components for different modules may be interspersed with each other such that each module may be defined by the set of connected components that collectively perform a predetermined function. However, the components of each module may or may not be physically grouped within the cartridge. In some embodiments, multiple cartridges may be used to process a single cell product through transfer of the cell product from one cartridge to another cartridge of the same or different type and/or by splitting cell product into more cartridges and/or pooling multiple cell products into fewer cartridges.

Generally, each of the instruments within the workcell interfaces with, or is releasably coupled to, its respective module or modules on the cartridge in order to carry out a specific cell processing step. For example, when a cartridge has an electroporation module, it may be moved by the robot to a bay within the workcell having an electroporation instrument within the workcell to perform electroporation on the cells within the cartridge. One advantage of such split module/instrument designs is that expensive components (e.g., motors, sensors, heaters, lasers, etc.) may be retained in the instruments of the system while less expensive components reside in the cartridge.

Figure 1B:
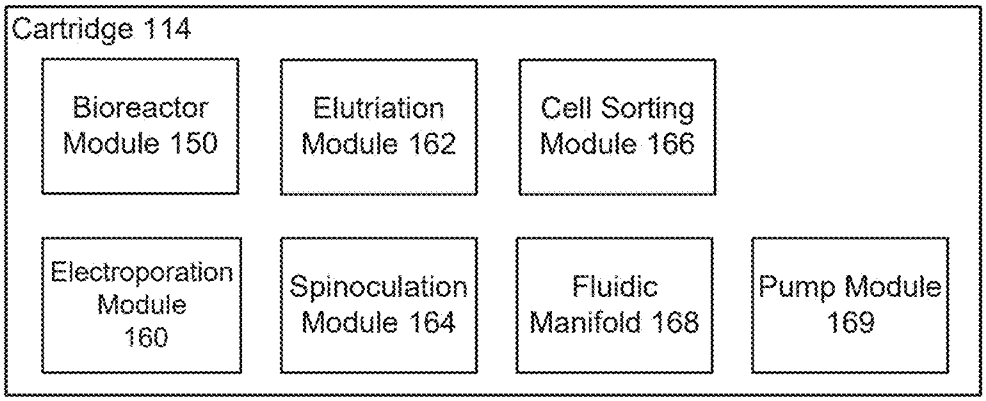
FIG. 1B is a block diagram of a cartridge that may be provided to the cell processing system of FIG. 1A.

As illustrated in FIG. 1B, the cartridge 114 may be configured to contain (e.g., house) a cell solution (e.g., cell suspension) for cell processing. Any number of cell processing steps may take place upon the cells within the cartridge. Accordingly, the cartridge 114 may comprise one or more of a bioreactor module 150, an electroporation module 160, an elutriation module 162, a spinoculation module 164, a cell sorting module 166, a fluidic manifold 168, and a pump module 169. The pump module 169 may be configured to pump one or more fluids to one or more modules of the cartridge 114. For example, the pump module 169 may pump a fluid to the fluidic manifold 168. In another example, the pump module 169 may pump a fluid (e.g., a cell solution) to the cell sorting module 166. The cell solution may include cellular material, including target cells coupled to magnetic particles. In another example, the pump module 169 may pump a fluid to the fluidic manifold 168, which may subsequently transfer a fluid to any other module, such as after a cell sorting process may have been performed.

The bioreactor module 150 may be configured to contain the cell solution. The bioreactor module 150 may further comprise a mixing chamber, in which the cell solution may be mixed with one or more reagents. The one or more reagents may comprise magnetic particles configured to couple to cells of a specific type (e.g., target cells). The elutriation module 162 may be configured to perform an elutriation process, wherein cellular material may be separated according to size, shape, and/or density. The spinoculation module 164 may be configured to perform a spinoculation process, wherein cells of different types may be bound together.

Other suitable cartridges and their cell processing modules that may be used with the automatic cell processing workcells described herein are provided in, e.g., U.S. Patent Application No. 63/464,386, U.S. Patent Application No. 63/427,720, U.S. Patent Application No. 63/456,388, and U.S. Patent Application No. 63/453,730, each of which is incorporated in their entirety by reference herein.

Figure 2A:
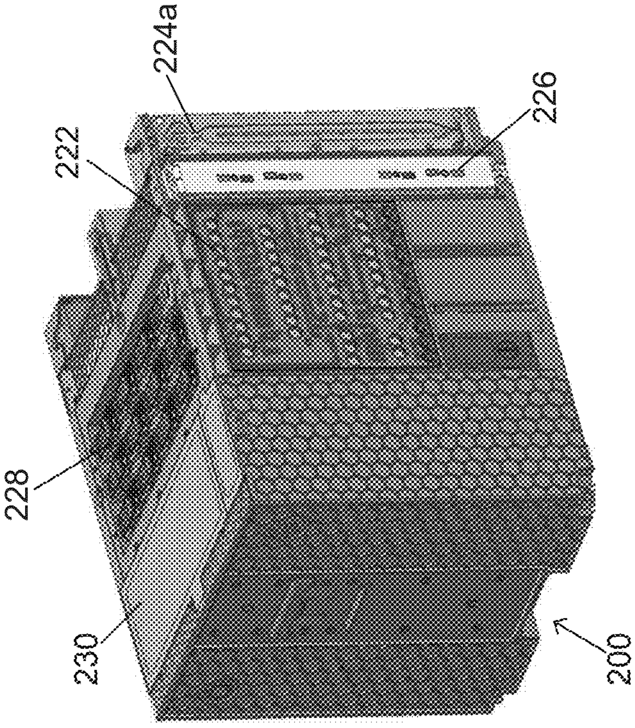
FIG. 2A is a front perspective view of an illustrative rendering of a cartridge that may be provided to a cell processing system.
Figure 2B:
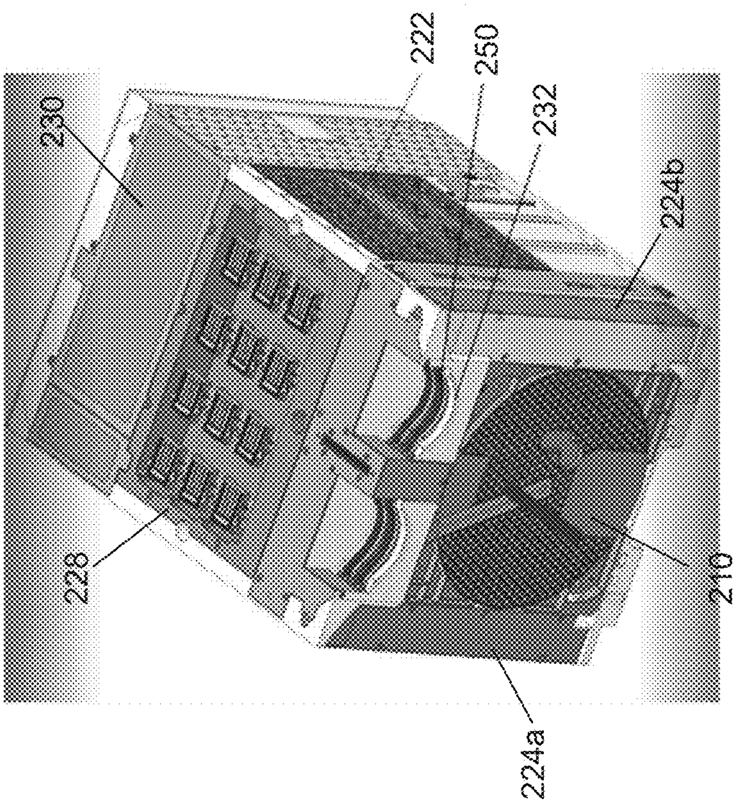
FIG. 2B is a rear perspective view of the cartridge shown in FIG. 2A.

Referring to FIGS. 2A and 2B, an illustrative variation of a cartridge 200 is shown. In this variation, cartridge 200 comprises an elutriation module 210, a fluidic manifold 222, a first cell sorting module **224*a*, a second cell sorting module 224*b*, an auxiliary module 226, a fluid device tray 228, a liquid container 230, and a pump module 232. While shown in these figures as having two cell sorting modules, it should be understood that any number of cell sorting modules may be used as desirable, and that the cartridge may be configured with any module as appropriate for a given cell processing workflow. For example, the cartridge may contain 1, 2, 3, 4, or even more cell sorting modules depending on the size of the cartridge, the existence of other cell processing modules within the cartridge, and so on. Additional modules may be added to the cartridge, or various modules may be exchanged for others. The cell sorting modules 224*a*, 224*b* may perform a magnetic cell sorting process. The electroporation module 220** may be configured to facilitate intracellular delivery of macromolecules (i.e., transfection by electroporation). An electrical discharge from one or more capacitors, or current sources, may generate sufficient current in the chamber to promote transfer of a polynucleotide, protein, nucleoprotein complex, or other macromolecule into the cells in the cell product.

The pump module 232 may have a pump configured to pump fluid in one or more directions along at least one fluid conduit 250. The at least one fluid conduit 250 of the pump module 232 may be configured to allow fluid to pass therethrough. For example, the fluid may be a liquid or a gas. In some variations, the fluid may comprise a solution of cells of varying sizes and densities. The pump module 232 may be fluidically connected to at least one module within the cartridge 200. Similarly, the pump module may be fluidically connected to one or more sterile liquid transfer devices. For example, the pump module 232 may be configured to pump a fluid to or from one or more of the elutriation module 210, the fluidic manifold 222, the cell sorting modules **224*a*, 224*b*, the auxiliary module 226, the fluid device tray 228, the liquid container 230, and any other module within the cartridge. The pump module 232 may be in communication with a controller, such as the controller 120 described in reference to FIG. 1A. For example, at least one rotor of the pump module 232 may rotate in response to a command sent by the controller 120** to transfer fluid to various modules of the cartridge in accordance with a pre-determined workflow.

The fluid transfer port tray 228 may comprise one or more ports configured to transfer fluid to or from one or more fluid devices. That is, each port of the fluid transfer port tray 228 may be configured to facilitate a sterile liquid transfer. In some variations, each port may be fluidically connected to a fluid conduit configured to fluidically connect with at least one module of the cartridge 114. For example, each port of the fluid transfer port tray 228 may be fluidically connected to the fluidic manifold 222. In this way, a fluid may flow from a fluid device coupled to a port of the fluid transfer port tray 228 to the fluidic manifold 222, or vice versa. In some variations, each port of the fluid transfer port tray 228 may be fluidically connected to the liquid storage container 230. The liquid storage container 230 may be configured to contain a fluid. In some variations, the fluid may be a liquid or a gas. In some variations, the liquid storage container 230 comprises a plurality of liquid containers. For example, the liquid storage container 230 may comprise one container, two containers, or three containers. The liquid storage container 230 may be fluidically connected to at least one module of the cartridge 200. In some variations, the liquid container 230 may be fluidically connected to the fluidic manifold 222. Accordingly, a fluid may flow between a port of the fluid transfer port tray 228, the fluidic manifold 222, and the liquid storage container 230.

The auxiliary module 226 may be configured to engage with at least one instrument and/or module. The auxiliary module 226 may comprise at least one electrical connector and/or at least one fluidic connector. In some variations, the auxiliary module 226 may be removed and replaced by any other module.

Various biocompatible materials may be used to construct the cartridge (including the modules thereof) and the cartridge housing, including metal, plastic, rubber, and/or glass, or combinations thereof. The cartridge, its components, and its housing may be molded, machined, extruded, 3D printed, or any combination thereof. The cartridge may contain components that are commercially available (e.g., tubing, valves, fittings). The commercially available components may be attached or integrated with custom components or devices. The housing of the cartridge may constitute an additional layer of enclosure that further protects the sterility of the cell product.

i. Pump Module

The pump modules for use with the cartridges described herein are configured to transfer fluid to and/or from one or more modules. In some variations, the fluid transfer between the one or more modules occurs at a predetermined flow rate. The pump modules may be configured to deliver a fluid (e.g., cell product(s)) to one or more modules according to a pre-defined workflow, which may be pre-programmed into a controller of a workcell as described herein throughout. The fluid may be a liquid or a gas. In some variations, the fluid may be a solution (e.g., a cell solution, a cell suspension). For example, the solution may comprise one or more of a cell, a media, a buffer, and a reagent. The pump module may comprise one or more pumps fluidically connected to the fluidic manifold, such as one or more of a direct lift pump, displacement pump, gravity pump, reciprocating pump, rotary pump, and peristaltic pump. In some embodiments, one or more of the instruments of the system comprise one or more integrated pump actuators. In this way, the engagement of the pump actuator of the instrument with the pump module of the cartridge may enable fluid flow to transfer fluid between modules, fluidic containers, or other components while the cartridge may be interfaced to that module. The system (e.g., workcell) may also comprise a dedicated pump instrument configured to interface with a pump module comprising a pump.

The pump module may be used to facilitate a cell processing step. For example, a sorting step may comprise sorting a population of cells in the solution by pumping the solution to a sorting module of the cartridge using the pump module, operating the robot to move the cartridge to a sorting instrument so that the sorting module may interface with the sorting instrument, and operating the sorting instrument to cause the sorting module to sort the population of cells.

In some variations, an enrichment step may comprise enriching a selected population of cells in a solution by pumping the solution to the elutriation module of the cartridge using the pump module, operating the robot to move the cartridge to an elutriation instrument so that the elutriation instrument may interface with the elutriation module, and operating the elutriation instrument to cause the elutriation module to enrich the selected population of cells.

In some variations, an expansion step may comprise expanding the cells in the solution by pumping the solution to the bioreactor module of the cartridge using the pump module, operating the robot to move the cartridge to the bioreactor instrument so that the bioreactor instrument interfaces with the bioreactor module, and operating the bioreactor instrument to cause the bioreactor module to allow the cells to expand by cellular replication.

In further variations, the pump module may pump fluid (e.g., solution) to the fluidic manifold, which may transfer the fluid to one or more modules. Fluidic manifolds that may be used with the pump modules described herein are provided in, e.g., U.S. Patent Application No. 63/520,859, which is incorporated in its entirety by reference herein.

Figure 1C:
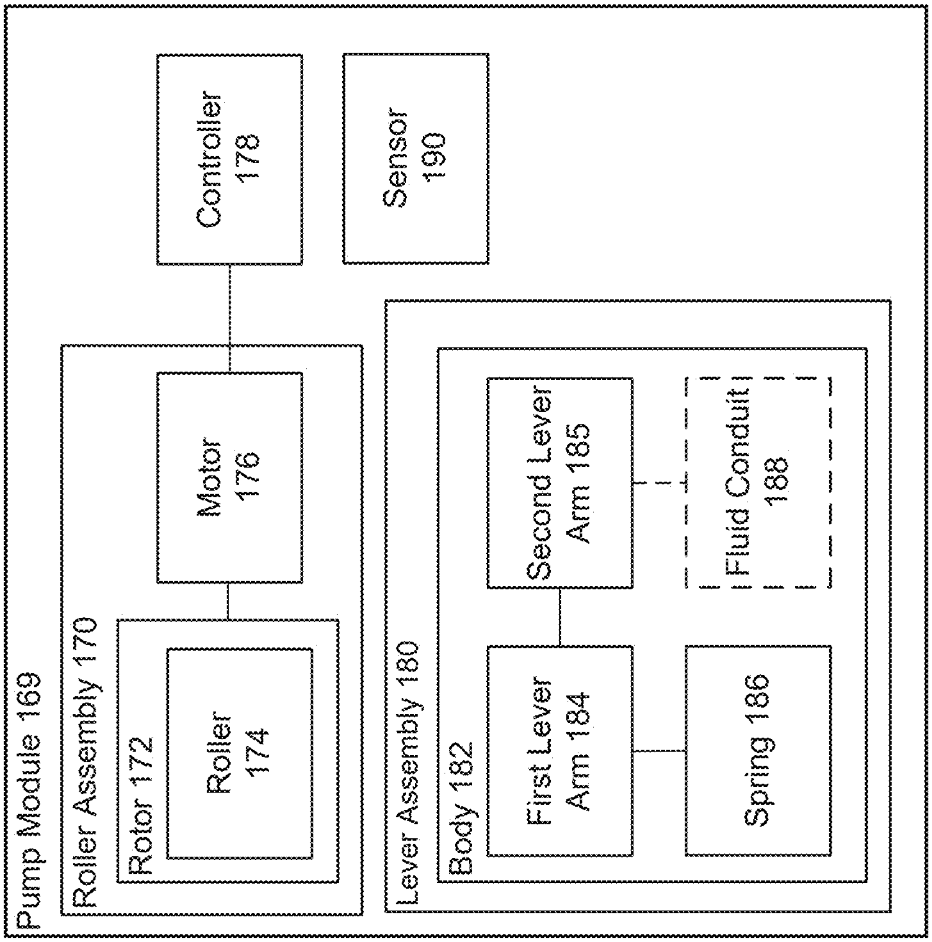
FIG. 1C is a block diagram of a pump module of the cartridge of FIG. 1B.

Referring to FIG. 1C, a block diagram of an exemplary variation of one suitable pump module 169 as described herein is shown. The pump module 169 may comprise a roller assembly 170 and a lever assembly 180. The roller assembly 170 may interact with the lever assembly 180 to pump a fluid to one or more modules and/or fluid transfer devices. For example, the roller assembly 170 may comprise a rotor 170 and a motor 176. The motor 176 may be operatively coupled to the rotor 170, such that the motor 176 may rotate (e.g., spin) the rotor 170 at a predetermined rate of rotation. In some variations, the rate of rotation may be between about 1 rotations per minute (RPM) and about 200 RPM, about 1 RPM and about 120 RPM, about 1 RPM and about 50 RPM, about 10 RPM and about 40 RPM, about 10 RPM and about 30 RPM, or about 10 RPM and about 20 RPM. In some variations, the rate of rotation of the rotor 170 may be up to about 5 RPM, about 10 RPM, about 20 RPM, or about 30 RPM. In an exemplary variation, the rate of rotation may be between about 1 RPM and about 20 RPM, including about 10 RPM.

The rotor 172 may comprise one or more features configured to engage with a fluid conduit (e.g., tube). For example, the rotor 172 may comprise one or more rollers 174. The rollers 174 may extend beyond an outer circumference of the rotor 172, such that rollers 174 may contact a fluid conduit, whereas the rotor 172 may avoid contacting a fluid conduit. However, in some variations, the rotor 172 may contact the fluid conduit without damaging the fluid conduit. The rollers 174 may form a seal with the fluid conduit when in contact therewith. The rollers 174 may comprise a curved surface configured to compress a fluid conduit without damaging the fluid conduit. For example, the roller may comprise a cross-sectional shape such as a circle, an oval, or any other shape with dulled edges configured to avoid damaging a fluid conduit. In some variations, the rotor 172 may comprise 1, 2, 3, 4, 5, 6, 7, 8, 9, 10, 11, 12, or more rollers, such as at least 3 rollers, at least 5 rollers, or between 6 and 10 rollers. In an exemplary variation, the rotor may comprise 8 rollers. In variations with more than one roller, the rollers 174 may be equally spaced apart along an outer circumference of the rotor 172, but need not be. In some variations, the rollers 174 may be fixedly attached to the rotor 172. In further variations, the rollers 174 may be configured to rotate relative to the rotor 172. For example, the rollers 174 may be coupled to the rotor 172 by an axle, such that the rollers 174 may freely rotate relative to the rotor 172. In some variations, the rollers 174 may be operatively coupled to the motor 176, such that the rollers 174 may be independently rotated at a predetermined rate of rotation via the motor 176. The rollers 174 may be manufactured from a plastic, a metal, a glass, or combination thereof. In an exemplary variation, the rollers 174 may be manufactured from a material that may be suitable to compress a soft plastic or rubber, which may be used to manufacture the fluid conduit as described herein.

The lever assembly 180 may comprise a body 182 configured to house one or more lever arms and/or fluid conduits. The body 182 may be fixedly attached to the cartridge 114. The body 182 may comprise a first lever arm 184, a second lever arm 185, a spring 186, and, optionally, a fluid conduit 188. The first lever arm 184 may be coupled to the body 182 by a mechanical fastener, such as a pin, a screw, a nail, or similar means. For example, in some variations, a pin (e.g., axle) may connect the first lever arm 184 to the body 182. The pin may define a first hinge. The first lever arm 184 may be configured to rotate about the first hinge, such that the first lever arm 184 may rotate relative to the body 182 about an axis of rotation defined by the hinge. The second lever arm 185 may be movably coupled to the first lever arm 184. For example, a pin (e.g., axle) may connect the second lever arm 185 to the first lever arm 184. The pin may define a second hinge. The second lever arm 185 may be configured to rotate about the second hinge, such that the second lever arm 185 may rotate relative to the first lever arm 184 and the body 182 about an axis of rotation defined by the second hinge.

The first lever arm 184 may have a shape similar to the second lever arm 185, or may have a different shape. The second lever arm 185 may be coupled to the first lever arm 184 in a manner that allows its movement. For example, the first lever arm 184 may define a rectangular shape with an opening configured to receive the second lever arm 185. In particular, the opening may have a length and/or a width greater than a length and/or a width of the second lever arm 185. In another example, the first lever arm 184 may define a U-shaped channel, such that the second lever arm 185 may be received within the U-shaped channel. The U-shaped channel may comprise a width greater than the width of the second lever arm 185. The U-shaped channel may comprise a depth such that the second lever arm 185 may rotate (e.g., tilt). In some variations, the first lever arm 184 may be formed by joining together two or more portions, such that a first portion of the first lever arm 184 is positioned adjacent to a first side of the second lever arm 185 and a second portion of the first lever arm 184 is positioned adjacent to a second side of the second lever arm 185. In any of the variations described herein, the second lever arm 185 may be configured to rotate between about 1 degree and about 80 degrees, such as about 5 degrees, about 10 degrees, about 20 degrees, about 30 degrees, about 40 degrees, about 50 degrees, about 60 degrees, about 70 degrees, or about 80 degrees relative to the body 182.

The second lever arm 185 may comprise a shape configured to receive a fluid conduit 188 and/or engage with the roller assembly 170. For example, the second lever arm 185 may comprise a beam that is straight or, in some variations, may be curved. The second lever arm 185 may be configured to align with the rotor 172, which may provide for consistent and/or predictable contact between the rotor and the fluid conduit and, accordingly, may advantageously facilitate a consistent flow rate. In some variations, a radius of curvature of the second lever arm 185 may be equivalent to or greater than a radius of curvature of the rotor 172. The respective radii of curvature may facilitate consistent spacing between the second lever arm 185 and the rotor 172. The consistent spacing may advantageously provide consistent contact between the rollers 174 and the fluid conduit 188. For example, the fluid conduit 188 may be releasably coupled at a proximal portion of the second lever arm 185 and/or a distal portion of the second lever arm 185. The second lever arm 185 may comprise a longitudinal dimension and a lateral dimension, where the longitudinal dimension may be greater than the later dimension. In some variations, a ratio of the longitudinal dimension to the lateral dimension may be between about 1.1:1 and about 6:1, including about 1.1:1, about 2:1, about 3:1, about 4:1, about 5:1, or about 6:1. The longitudinal dimension of the second lever arm 185 may correspond to an arc length of contact between the rollers 174 and the fluid conduit 188, as will be described further below.

The pump module 169 may be configured to pump fluid through one or more fluid pathways (e.g., the fluid conduit 188). For example, in some variations, the pump module 169 may comprise 1, 2, 3, 4, 5, 6, 7, 8, 9, 10, or more fluid conduits. The fluid conduit 188 may be coupled to one or more lever arms. For example, the fluid conduit 188 may be releasably coupled to the second lever arm 185. In some variations, more than one fluid conduit 188 may be releasably coupled to a single lever arm. For example, two fluid conduits 188 may be releasably coupled to the second lever arm 185, such that each fluid conduit 188 may be compressed simultaneously by the same roller assembly 170. In some variations, more than one roller assembly may be used to compress more than one fluid conduit 188. For example, a first fluid conduit may be compressed by a first roller assembly and a second fluid conduit may be compressed by a second roller assembly. The first and second roller assemblies may be rotated synchronously or asynchronously. For example, the first and second roller assemblies may share an axle, such that each roller assembly may be controlled by the same motor and rotate at the same rate of rotation in the same direction of rotation. In another example, the first and second roller assemblies may be coupled to different axles, such that each roller assembly may be independently controlled by different motor and may, or may not, rotate at the same rate of rotation. Accordingly, the fluid conduit 188 may comprise a compressible material, such as a plastic, a rubber, or a combination thereof.

The rate of rotation may be proportional to a flow rate through the fluid conduit 188. For example, an increase in the rate of rotation of the rotor 172 may result in an increased flow rate, and vice versa. In some variations, the flow rate through the fluid conduit 188 may be predetermined according to a workflow that has been preprogrammed into a controller of the workcell. In this way, different flow rates may be set depending on the module to be utilized. However, the flow rates need not be different. For example, the fluid may be pumped at the same or different flow rates to a module configured for cell sorting, elutriation, spinoculation, precise dosing, or combinations thereof. Accordingly, in some variations, the flow rate through the fluid conduit 188 may be between about 0.1 mL/min and about 30 mL/min, about 1 mL/min and about 30 mL/min, about 2 mL/min and about 20 mL/min, about 5 mL/min and about 15 mL/min, or about 8 mL/min and about 12 mL/min, including about 0.1 mL/min, about 1 mL/min, about 2 mL/min, about 5 mL/min, about 8 mL/min, about 10 mL/min, about 15 mL/min, or about 12 mL/min. In an exemplary variation, the flow rate may be about 10 mL/min or less.

The pump module 169 may be optimized to maintain consistent contact between rollers 174 and the fluid conduit 188 using the spring 186. The spring 186 may be coupled to the first lever arm 184. For example, the spring 186 may be coupled to a distal portion of the first lever arm 184. The spring 186 may be configured to limit the rotation of the first lever arm 184 around the first hinge. The spring 186 may elastically deform when a force may be applied to the lever assembly, such as a compressive force applied by the roller assembly 170 to the fluid conduit 188 of the lever assembly 180. For example, the rollers 174 may apply a compressive force to the fluid conduit 188 coupled to the second lever arm 185, which may transfer at least a portion of the force to the first lever arm 184. Accordingly, one or more of the first and second lever arms 184, 185 may move (e.g., rotate) in response to the compressive force applied by the rollers 174. In some variations, the spring 186 may be used to absorb a vibrational load. For example, one or more cell processing steps performed by one or more modules of the cartridge 114 may cause vibrations, which may otherwise cause the rollers 174 to lose contact with the fluid conduit 188. Therefore, in some variations, the spring 186 may comprise a spring force between about 1 N and about 100 N, about 5 N and about 50 N, about 10 N and about 40 N, or about 20 N and about 30 N, such as about 1 N, about 5 N, about 10 N, about 20 N, about 25 N, or about 30 N. In an exemplary variation, the spring 186 may comprise a spring force of about 25 N, which may advantageously facilitate consistent contact between the rollers 174 and the fluid conduit 188 by resisting and/or correcting misalignments in a horizontal and/or vertical direction of the second lever arm 185 relative to the rollers 174 and/or rotor 172.

In some variations, a sensor 190 may be utilized to measure one or more parameters of the roller assembly 170 and/or lever assembly 180. For example, in some variations, the sensor 190 may comprise one or more of a position sensor, a motor sensor, a force sensor, a flow rate sensor, an optical sensor, or combination thereof. For example, the sensor 190 may comprise a position sensor configured to measure a position of one or more of the rollers 174 and rotor 172. In some variations, the position sensor may be operatively coupled to the rotor 172. In further variations, the position sensor may be adjacent to the rotor 172 such that it may detect one or more features of the rotor 172. Advantageously, the position measurements of the rollers 174 and/or rotor 172 may be used to determine a rate of rotation and/or a direction of rotation of the rotor 172. In another example, the sensor 190 may comprise a motor sensor configured to measure one or more of a torque value, a current value, and a voltage value of the motor 176. The motor sensor may be operatively coupled to the motor 176. The one or more measurements by the motor sensor may be used to determine a rate of rotation of the rotor 172. In another example, the sensor 190 may comprise a flow rate sensor configured to measure a flow rate at an inlet and/or an outlet of the fluid conduit 188. The flow rate sensor may be coupled to an inlet or outlet of the fluid conduit 188. The measured flow rate(s) may be used to determine a rate of rotation of the rotor. The sensor 190 may be configured to measure one or more parameters continuously or discontinuously. Such data can be used in conjunction with known characteristics of the fluid conduits 188, such as a material, a length, and a diameter. In some variations, the data may further include properties (e.g., viscosity) of the fluid to be transferred.

When a sensor 190 is utilized, the measurements may be used to modify one or more operating parameters of the pump module 169, either in a closed or open loop fashion. For example, the controller 178 (e.g., an encoder) may be configured to modify the rate of rotation of the rotor 172 in response to one or more sensor measurements. In some variations, the controller 178 may be electrically connected to the sensor 190, such that the controller 178 may modify the rate of rotation of the rotor 172 based on one or more measurements by the sensor 190. For example, the controller 178 may be electrically connected to the motor 176, such that the controller may adjust the status (e.g., on, off) and/or electrical parameters (e.g., voltage, current) of the motor 176. Adjustments made to the motor 176 via the controller 178 may, in turn, modify the rate of rotation of the rotor 172 and/or flow rate through the fluid conduit 188. For example, the flow rate through the fluid conduit 188 may be directly proportional to the rate of rotation of the rotor 172. Accordingly, increasing the rate of rotation of the rotor 172 may increase the flow rate through the fluid conduit 188 and, conversely, decreasing the rate of rotation of the rotor 172 may decrease the flow rate through the fluid conduit 188. The controller 178 may operate the pump module 169 in a closed loop or an open loop manner, as described further below.

Figure 3:
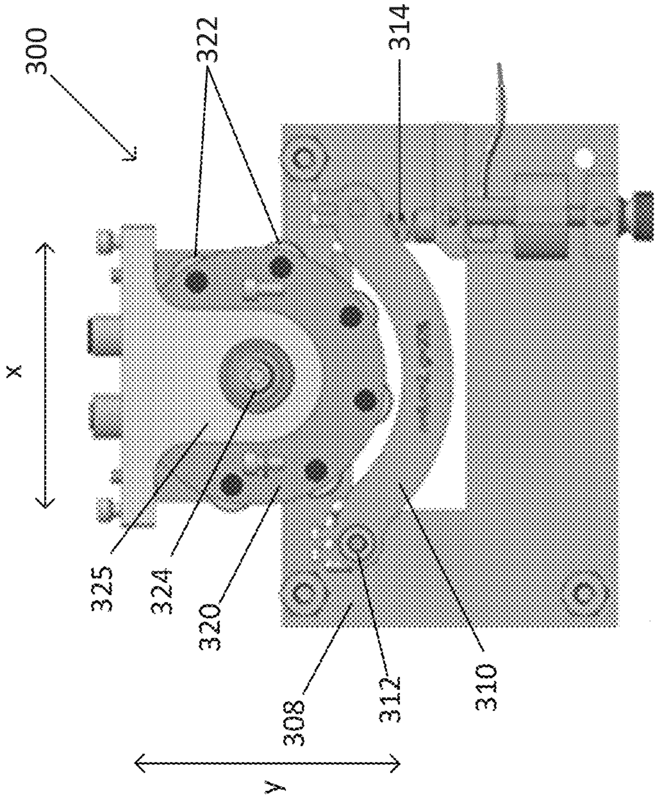
FIG. 3 is a front view of a rendering of a pump module of a cartridge comprising a fluid pumping device.

FIG. 3 illustrates an exemplary variation of a pump module 300. The pump module 300 may comprise a body 308, a lever arm 310, a spring 314, and a rotor 320. The lever arm 310 may be coupled to the body 308 by a hinge 312. The hinge 312 may be positioned at a proximal portion of the lever arm 310. The hinge 312 may comprise a pin that extends through the lever arm 310 parallel to a lateral dimension thereof. The hinge 312 may define a pivot point for the lever arm 310. For example, the lever arm 310 may rotate about the hinge 312 in response to a compressive force. The compressive force may be resisted by the spring 314. The spring 314 may be positioned at a distal portion of the lever arm 310. For example, the spring 314 may elastically deform in response to the compressive force. A fluid conduit (not shown) may be coupled to the lever arm 310. For example, the fluid conduit may be coupled to a proximal portion and/or a distal portion of the lever arm 310.

The pump module 300 may pump fluid by rotating one or more components. For example, the rotor 320 may be coupled to a rotor mount 325 by an axle 324. The rotor 320 may rotate about the axle 324 in a clockwise direction and/or a counterclockwise direction. In some variations, the rotor mount 325 may be coupled to a pump instrument (not shown) of a workcell. As another example, the rotor 320 may comprise a plurality of rollers 322 which may be configured to apply the compressive force to a fluid conduit (not shown) such that fluid may be pumped therethrough. The plurality of rollers 322 may be evenly spaced around a circumference of the rotor 320. In other variations, the plurality of rollers 322 may be distributed unevenly around a circumference of the rotor 320. As shown, each of the plurality of rollers 322 may protrude from an outer surface of the rotor 320. The lever arm 310 and, optionally, the fluid conduit, may be concentrically aligned with the rotor 320. Maintaining concentric alignment between the second lever arm 310 and the rotor 320 may facilitate proper functionality of the pump module 300 by ensuring consistent contact between the plurality of rollers 322 and the fluid conduit along a longitudinal dimension of the lever arm 310. The rotor 320 may be positioned at a midpoint of a longitudinal dimension of the lever arm 310. The position of the rotor 320 relative to the lever arm 310 may facilitate fluid pumping. For example, the plurality of rollers 322 may be configured to compress a fluid conduit (not shown) that may be received by and/or coupled to the lever arm 310. The compressive force applied by the rollers 322 may cause the lever arm 310 to move along a y-axis, which may compress the spring 314. Accordingly, the spring 314 may resist the movement of the lever arm 310, which may facilitate sufficient contact between the fluid conduit (not shown) and the plurality of rollers 322 during rotation of the rotor 320.

An alternative design of a pump module 400 is also described herein. For example, with reference now to FIG. 4, the pump module 400 comprises a body 408, a first lever arm 410, a second lever arm 416, a spring 414, and a rotor 420. The first lever arm 410 may be coupled to the body 408 by a first hinge 412. The first hinge 412 may be positioned at a proximal portion of the first lever arm 410. The first hinge 412 may comprise a pin that extends through the first lever arm 410 parallel to a lateral dimension thereof. The first hinge 412 may define a pivot point for the first lever arm 410. For example, the first lever arm 410 may rotate about the hinge 412 in response to a compressive force. For example, the compressive force may be applied by the rotor 420 to a fluid conduit (not shown), such as when the rotor 420 may be moved towards the lever arm 410 along a y-axis. The compressive force may be resisted by the spring 414. The spring 414 may be positioned at a distal portion of the first lever arm 410. For example, the spring 414 may elastically deform in response to the compressive force. In some variations, the spring 414 may be configured to accommodate a deflection of the first lever arm 410 and/or second lever arm 416 in any of an x-axis, y-axis, or z-axis. For example, such a deflection may correspond to the compressive force applied by the rotor 420.

Additional functionality may be facilitated by one or more additional rotatable components. For example, the rotor 420 may be coupled to a rotor mount 425 by an axle 424. The rotor 420 may rotate about the axle 424 in a clockwise direction and/or a counterclockwise direction. In some variations, the rotor mount 425 may be coupled to a pump instrument (not shown) of a workcell. As another example, as shown, the first lever arm 410 may further comprise a second hinge 418. The second lever arm 416 may be coupled to the first lever arm 410 via the second hinge 418. The second hinge 418 may define a pivot point for the second lever arm 416. For example, the second lever arm 416 may rotate about the second hinge 418 in response to the compressive force applied to the fluid conduit (not shown). The second hinge 418 may be positioned between the proximal and distal portions of the first lever arm 410. In some variations, the second hinge 418 may be positioned equidistantly between the proximal and distal portions of the first lever arm 410. The second hinge 418 may comprise a pin that extends through the second lever arm 416 parallel to a lateral dimension thereof.

Figure 4:
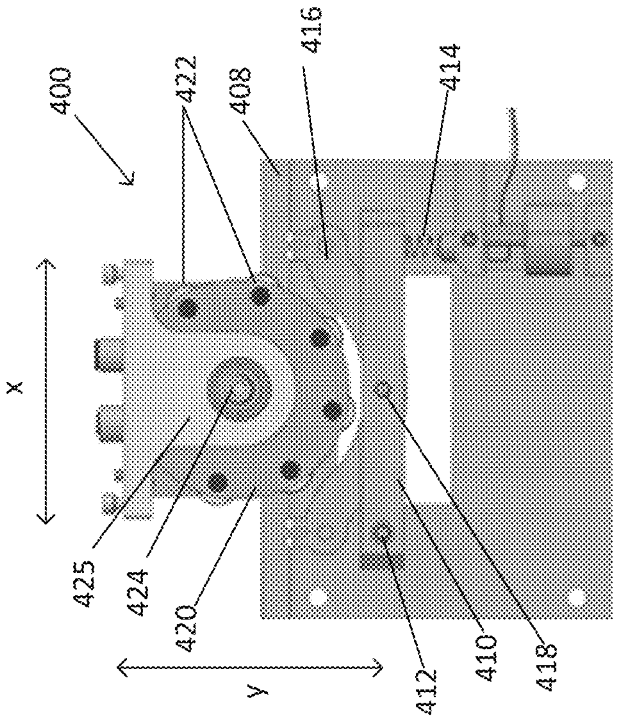
FIG. 4 is a front view of another rendering of an illustrate pump module of a cartridge comprising a fluid pumping device.

The pump module 400 may pump fluid by rotating one or more components and may be configured to accommodate a misalignment between one or more components. For example, as shown, the rotor 420 may further comprise a plurality of rollers 422. The description of the rotor 420 and plurality of rollers 422 may correspond to the description provided in reference to elements 320 and 322 of FIG. 3. The second lever arm 416 may be configured to be concentrically aligned with the rotor 420. Maintaining concentric alignment between the second lever arm 416 and the rotor 420 may help facilitate proper functionality of the pump module 400. In particular, the concentric alignment may provide for consistent contact between the plurality of rollers 422 and the fluid conduit along a longitudinal dimension of the second lever arm 416. Furthermore, the second lever arm 416 may be configured to accommodate a misalignment with the rotor 420 by rotating about the second hinge 418. For example, as illustrated in FIG. 4, the misalignment may correspond to the rotor 420 positioned in either direction along the x-axis. The second lever arm 416 may be configured to rotate about the second hinge 418 such that the misalignment of the rotor 420 along the x-axis can be accommodated. In particular, the second lever arm 416 may rotate such that the plurality of rollers 422 may maintain contact with the fluid conduit (not shown) during rotation of the rotor 420. For example, in some variations, the second lever arm 416 may be configured to accommodate a misalignment of about 0.1 mm to about 10 mm, about 0.5 mm to about 4 mm, about 1 mm to about 3 mm, or about 1 mm to about 2 mm, including about 0.1 mm, about 0.5 mm, about 1 mm, about 2 mm, about 3 mm, about 4 mm, or about 5 mm. In an exemplary variation, the second lever arm 416 may be configured to accommodate a misalignment of about 2 mm.

Figure 13:
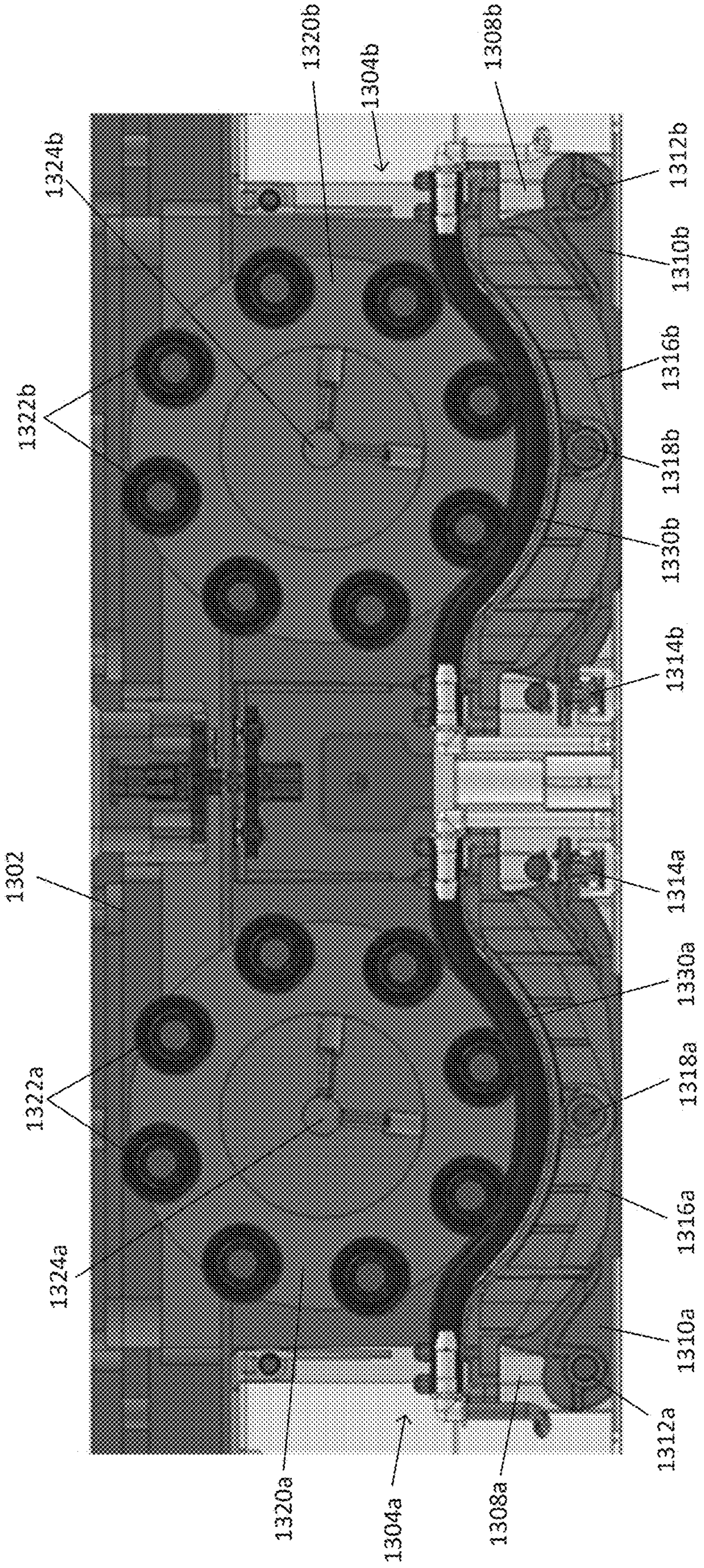
FIG. 13 is a front view of a rendering of an illustrative variation of a pump module of a cartridge and an instrument.

The pump modules described herein may be configured to engage with an instrument of a workcell. For example, FIG. 13 illustrates an exemplary variation of a first pump module 1304*a* and a second pump module 1304*b* that are each operatively coupled to an instrument 1302 of a workcell. The instrument 1302 may comprise a pump actuator configured to actuate one or more components of the pump modules 1304*a*, 1304*b* such that fluid may be pumped through one or more fluid conduits thereof. Similar to the descriptions provided for the pump module 400 in reference FIG. 4, the pump modules 1304*a*, 1304*b* may respectively comprise a rotor 1320*a*, 1320*b*, a first lever arm 1310*a*, 1310*b*, a second lever arm 1316*a*, 1316*b*. The rotors 1320*a*, 1320*b* may each comprise a plurality of rollers 1322*a*, 1322*b*. The first lever arms 1310*a*, 1310*b* may each comprise a first hinge 1312*a*, 1312*b* and a second hinge 1318*a*, 1318*b*. The first hinges 1312*a*, 1312*b* may be positioned at a first end of each of the first lever arms 1310*a*, 1310*b*. The second lever arms 1316*a*, 1316*b* may be coupled to the first lever arms 1310*a*, 1310*b* via the second hinges 1318*a*, 1318*b*. Coupled to a second end of each of the first lever arms 1310*a*, 1310*b* may be a spring 1314*a*, 1314*b*, respectively. As shown in FIG. 13, the second hinges 1318*a*, 1318*b* may be positioned between the first and second ends of the first lever arms 1310*a*, 1310*b*. The first hinges 1312*a*, 1312*b*, second hinges 1318*a*, 1318*b*, and springs 1314*a*, 1314*b* may correspond to the descriptions provided for elements 412, 418, and 414 in reference to FIG. 4. The pump modules 1304*a*, 1304*b* may further comprise a fluid conduit 1330*a*, 1330*b*. As shown, the fluid conduits 1330*a*, 1330*b* may be operatively coupled to the second lever arms 1316*a*, 1316*b*, respectively. The fluid conduits 1330*a*, 1330*b* and/or second lever arms 1316*a*, 1316*b* may be concentrically aligned with the rotors 1320*a*, 1320*b* and plurality of rollers 1322*a*, 1322*b*, respectively. Each of the rotors 1320*a*, 1320*b* may be coupled to an axle 1324*a*, 1324*b*. The axles 1324*a*, 1324*b* may define an axis of rotation for the rotors 1320*a*, 1320*b*. The rotors 1320*a*, 1320*b* may be configured to rotate in either of a clockwise or counterclockwise direction about the axles 1324*a*, 1324*b*. In some variations, the rotors 1320*a*, 1320*b* may rotate in the same direction as each other, but need not. That is, each of the rotors 1320*a*, 1320*b* may be independently controlled by a pump actuator (e.g., motor). The pump actuator (not shown) may be housed within an instrument, such as the instrument 1302.

The instrument 1302 may be configured to operatively couple to one or more of the pump modules 1304*a*, 1304*b*. For example, a cartridge comprising the pump modules 1304*a*, 1304*b* may be moved such that the pump modules 1304*a*, 1304*b* may be releasably coupled to the instrument 1302. Accordingly, the instrument 1302 may be configured to actuate the rotors 1320*a*, 1320*b* such that fluid may be pumped through one or more of the fluid conduits 1330*a*, 1330*b*. In some variations, the rotors 1320*a*, 1320*b* may be part of the instrument 1302. In such a variation, the rotors 1320*a*, 1320*b* may be moved in one or more directions, via the instrument 1302, such that the rotors 1320*a*, 1320*b* contact the fluid conduits 1330*a*, 1330*b*. The cartridge and/or instrument 1302 may be moved according to a predetermined workflow, such as by a robot. The instrument 1302 may comprise one or more of an electrical, a mechanical, and a fluidic connection with one or more of the pump modules 1304*a*, 1304*b*. For example, an electrical connection between the instrument 1302 and one or more of the pump modules 1304*a*, 1304*b* may be used to provide one or more electrical signals to the rotors 1320*a*, 1320*b* and/or may be used to receive one or more measurements from a sensor coupled to any part of the pump modules 1304*a*, 1304*b*. A mechanical fastener (e.g., pin, screw, adhesive, magnet) may be used to releasably couple the instrument 1302 to each of the pump modules 1304*a*, 1304*b*. In some variations, there may be a fluidic connection between the instrument 1302 and the fluid conduits 1330*a*, 1330*b*. Accordingly, the instrument 1302 may be useful in pumping fluid through one or more of the fluid conduits 1330*a*, 1330*b* by actuating (e.g., rotating) one or more of the rotors 1320*a*,

1320*b* such that the plurality of rollers 1322*a*, 1322*b* may compress the fluid conduits 1330*a*, 1330*b*. While two pump modules are illustrated in FIG. 13, the instrument 1302 may be configured to receive only one pump module or more than two pump modules simultaneously. For example, the instrument 1302 may be configured to receive 3, 4, 5, 6, 7, 8, 9, 10, or more pump modules, each of which may be coupled to the same cartridge or different cartridges. As shown in FIG. 13, the pump modules 1304*a*, 1304*b* may be arranged such that the pump modules 1304*a*, 1304*b* may be collinear with each other, but the pump modules 1304*a*, 1304*b* may be arranged in any orientation or configuration suitable for coupling with the instrument 1302.

Figure 5A:
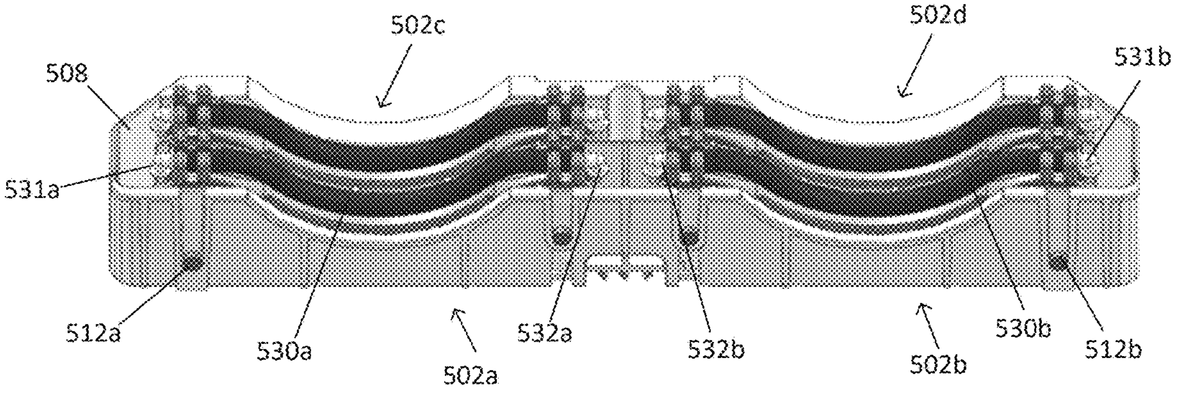
FIG. 5A is a front perspective view of a rendering of a lever assembly of a fluid pumping device of a pump module.
Figure 5B:
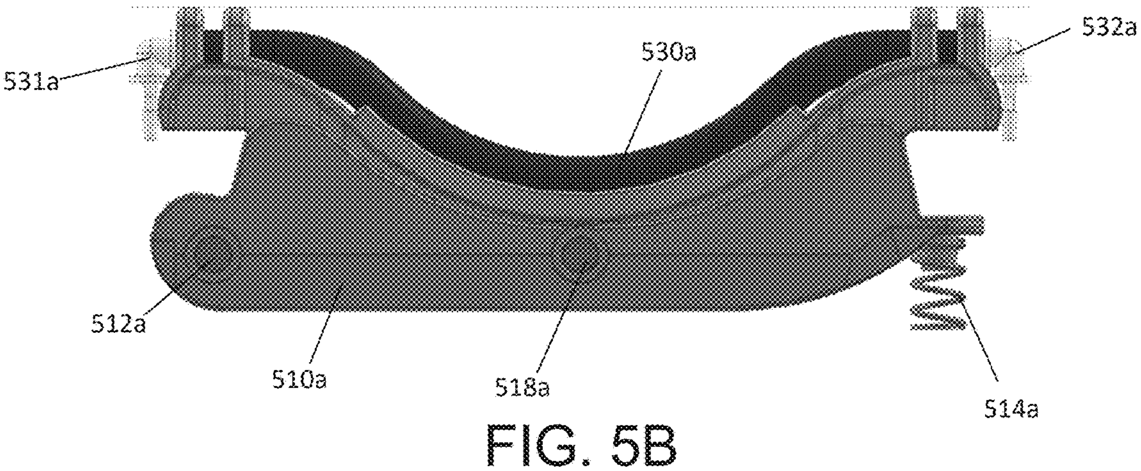
FIG. 5B is a front view of a portion of the lever assembly shown in FIG. 5A.
Figure 5C:
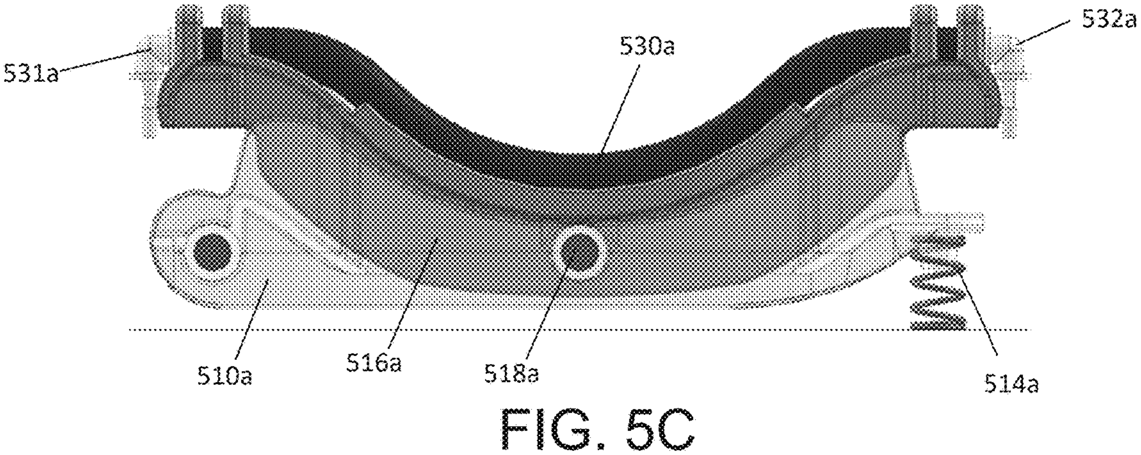
FIG. 5C is a front cross-sectional view of the portion of the lever assembly shown in FIG. 5B.

FIGS. 5A-5C illustrate an exemplary variation of a lever assembly 500. In this variation, the lever assembly 500 comprises a plurality of lever arms and fluid conduits. For example, as shown in FIGS. 5A-5C, the lever assembly 500 may comprise a body 508, a first lever sub-assembly 502*a*, a second lever sub-assembly 502*b*, a third lever sub-assembly 502*c*, and a fourth lever sub-assembly 502*d*. The first lever sub-assembly may comprise a first lever arm 510*a*, a second lever arm 516*a*, and a fluid conduit 530*a*. The first lever arm 510*a* may be coupled to the body 508 by a first hinge 512*a*, similar to the descriptions provided for the elements 410 and 412, respectively, in reference to FIG. 4. The second lever arm 516*a* may be coupled to the first lever arm 510*a* by a second hinge 518*a*, similar to the descriptions provided for the elements 416 and 418, respectively, in reference to FIG. 4. The fluid conduit 530*a* may be releasably coupled to the second lever arm 516*a*. Accordingly, the fluid conduit 530*a* may move in tandem with movement of the second lever arm 516*a*, such as in response to a compressive force applied by a plurality of rollers (not shown). The fluid conduit 530*a* may be coupled to an inlet conduit 531*a* and an outlet conduit 532*a*. The inlet and/or outlet conduits 531*a*, 532*a* may be fluidically connected to one or more modules, sterile liquid transfer devices, and fluidic manifolds. For example, the inlet conduit 531*a* may be configured to receive fluid from an external fluid source and/or the outlet conduit 532*a* may be configured to provide fluid to an external fluid source, or vice versa.

Each of the lever sub-assemblies may comprise similarly sized components configured to perform similar functions. For example, the second lever sub-assembly 502*b* may comprise a first lever arm 510*b*, a second lever arm 516*b*, and a fluid conduit 530*b*, which may correspond to the descriptions provided for each respective component of the first lever sub-assembly 502*a*. The lever sub-assemblies may be positioned relative to each other to facilitate pumping fluid at the same or different times. For example, the third lever sub-assembly 502*c* may be positioned adjacent to the first lever sub-assembly 502*a*. That is, the first lever arm 510*a* of the first lever sub-assembly 502*a* may be in contact with a first lever arm (not shown) of the third lever sub-assembly 502*c*. Accordingly, the first and third lever sub-assemblies 502*a*, 502*c* may be parallel to each other. In some variations, more than two lever sub-assemblies may be positioned next to one another. For example, in some variations, 2, 3, 4, 5, 6, 7, 8, 9, 10, or more lever sub-assemblies may be positioned next to each other. The fluid inlets and/or outlets of the fluid conduits of each of the lever sub-assemblies may be fluidically connected, but need not be.

A roller assembly (not shown) may be configured to engage with each of the lever sub-assemblies 502*a*-502*d*. For example, a first roller assembly comprising a first rotor with a plurality of rollers may be received by the first lever sub-assembly 502*a* and a second roller assembly comprising a second rotor with a plurality of rollers may be received by the third lever sub-assembly 502*c*. The first and second roller assemblies may be configured to rotate at the same rate of rotation. For example, the first and second roller assemblies may share an axle, such that a single motor may be configured to rotate the shared axle and, by extension, each of the first and third lever sub-assemblies 502*a*, 502*c*. In another example, the first and second roller assemblies may be coupled to different axles, such that separate motors may be used to rotate each axle and, by extension, each of the first and third lever sub-assemblies 502*a*, 502*c*. In such a configuration, first and second roller assemblies may rotate at the same or different rates of rotation. In some variations, the first roller assembly may engage with each of the first and third lever sub-assemblies 502*a*, 502*c*. In particular, the first roller assembly may contact the fluid conduits of each of the first and third lever sub-assemblies 502*a*, 502*c* simultaneously.

Figure 6:
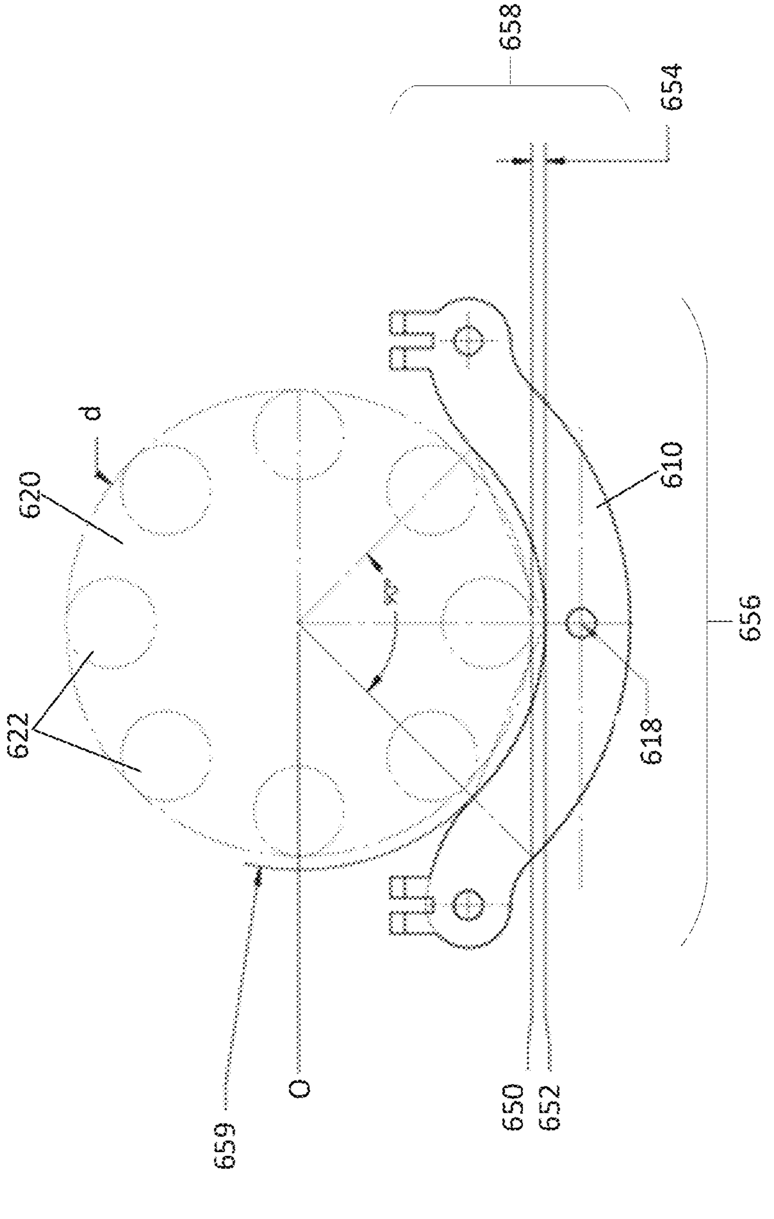
FIG. 6 is a of a schematic of an illustrative pump module.

FIG. 6 illustrates dimensions of an exemplary variation of a pump module 600. Similar to the other pump modules described herein, the pump module 600 may comprise a lever arm 610 and a rotor 620 comprising a plurality of rollers 622. The plurality of rollers 622 may be positioned along an outer edge of the rotor 620, and may be equally spaced thereabout (but need not be). The lever arm 610 and rotor 620 may each be appropriately sized to engage with each other. For example, the lever arm 610 may comprise a hinge 618, a length 656, a height 658, and a radius of curvature 659 that correspond to a diameter (d) of the rotor 620. The hinge 618 may be collinear with an origin, O, of the rotor 620, but need not be. The length 656 may be between about 10 mm and about 150 mm, about 20 mm and about 140 mm, about 50 mm and about 130 mm, or about 80 mm and about 120 mm. In an exemplary variation, the length 656 may be about 110 mm. The height 658 may be between about 5 mm and about 50 mm, about 10 mm and about 40 mm, or about 15 mm and about 35 mm. In an exemplary variation, the height 658 may be about 30 mm. The radius of curvature 659 may be between about 10 rad/mm and about 100 rad/mm, about 20 rad/mm and about 75 rad/mm, about 30 rad/mm and about 60 rad/mm, or about 40 rad/mm and about 45 rad/mm. In an exemplary variation, the radius of curvature 659 may be about 44 rad/mm. Meanwhile, the rotor may comprise a diameter (d) that may be between about 10 mm and about 150 mm, about 10 mm and about 120 mm, about 30 mm and about 100 mm, about 60 mm and about 90 mm, or about 80 mm and about 85 mm. In an exemplary variation, the diameter (d) may be about 82.55 mm. The diameter (d) may be equal to or less than the radius of curvature 659 of the lever arm 610, which may advantageously facilitate consistent spacing between the rotor 620 and the lever arm 610.

The rotor and lever arm may be separated by a distance, such that a fluid conduit positioned therebetween may be intermittently compressed. For example, an outer surface of the rotor and/or roller may be a distance 650 from the origin, O, of the rotor and an upper surface of the lever arm may be a distance 652 from the origin, O. A distance 654 (e.g., gap) between the rotor and the lever arm may be determined by the difference between the distances 650 and 652. For example, in some variations, the distance 654 may be between about 1 mm and about 10 mm, about 1 mm and about 8 mm, about 1 mm and about 6 mm, about 2 mm and about 4 mm, or about 2 mm and about 3 mm. In an exemplary variation, the distance may be about 2.4 mm.

Figure 7A:
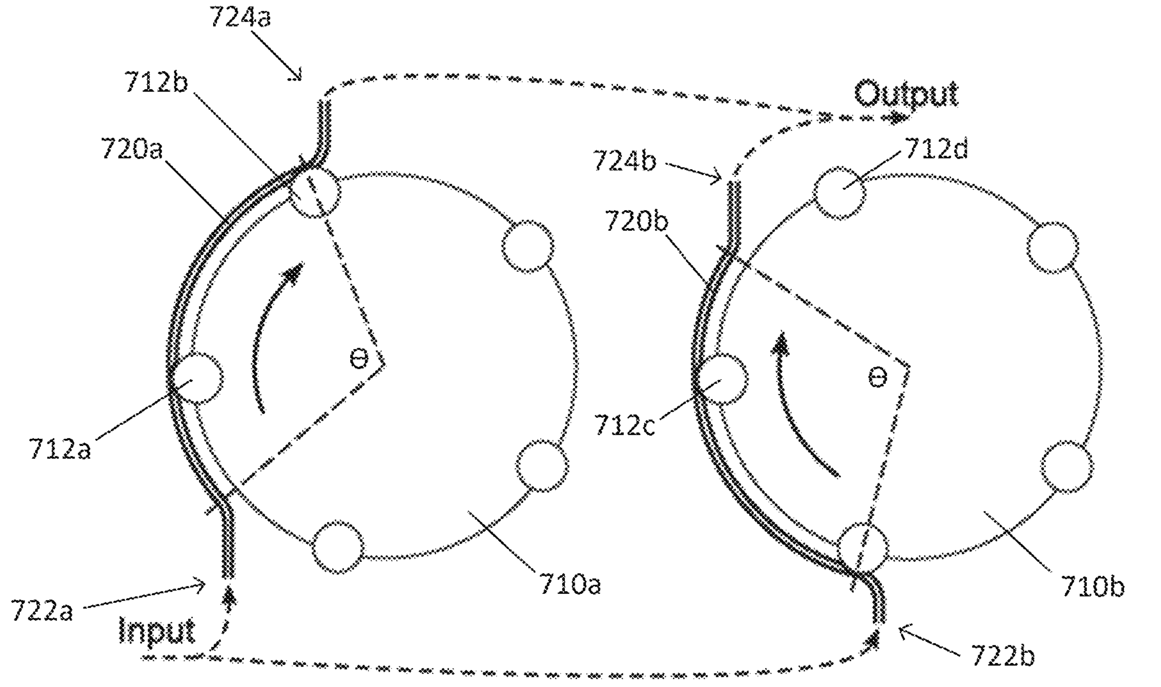
FIG. 7A is a front view of an illustrative variation of a fluid pumping device of a pump module in a first configuration.
Figure 7B:
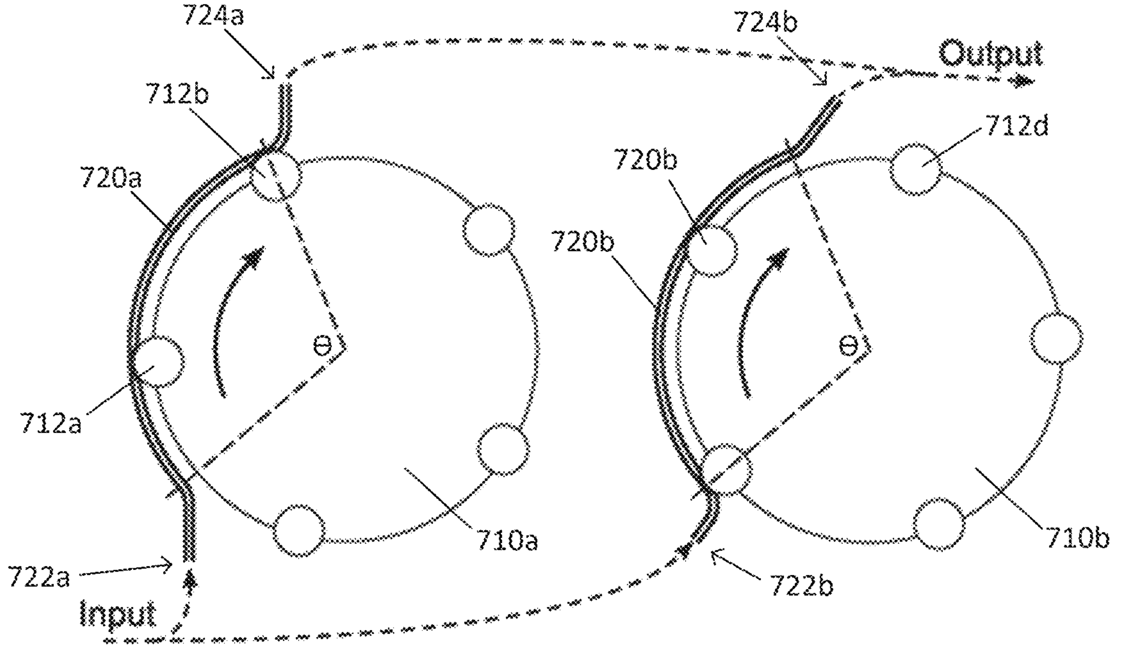
FIG. 7B is a front view of another illustrative variation of a fluid pumping device of a pump module in a second configuration.

FIGS. 7A and 7B illustrate exemplary variations of pump modules in different configurations. For example, FIG. 7A illustrates a first configuration of each of a first rotor 710*a* operatively coupled to a first fluid conduit 720*a* and a second rotor 710*b* operatively coupled to a second fluid conduit 720*b*. Each of the rotors 710*a*, 710*b* may comprise a plurality of rollers. As shown, the first rotor 710*a* may comprise a first roller 712*a* and a second roller 712*b* and, similarly, the second rotor 710*b* may comprise a third roller 712*c* and a fourth roller 712*d*. The first and second rollers 712*a*, 712*b* may contact the first fluid conduit 720*a* during rotation of the first rotor 710*a*. Due to the curved shape of the rotors 710*a*, 710*b*, the rollers 712*a*, 712*b* may stay in contact with the first fluid conduit 720*a* for an arc length of the rotor 710*a* corresponding to an angle θ and, similarly, the rollers 712*c*, 712*d* may stay in contact with the second fluid conduit 720*b* for an arc length corresponding to the angle θ. The angle θ may correspond to a length of a lever arm (not shown). For example, in some variations, the angle θ may be between about 5 degrees and about 180 degrees, about 10 degrees and about 150 degrees, about 40 degrees and about 120 degrees, about 60 degrees and about 120 degrees, or about 80 degrees and about 100 degrees, including about 10 degrees, about 30 degrees, about 50 degrees, about 70 degrees, about 90 degrees, or about 110 degrees. The rotors 710*a*, 710*b* may be configured to rotate synchronously (e.g., at the same rate of rotation), such that the rollers thereof maintain similar positions relative to each other. For example, as shown, the rollers 712*a* and 712*c* may be collinear with respect to each other and the rollers 712*b* and 712*d* may be collinear with respect to each other.

The flow through the fluid conduits 720*a*, 720*b* may be combined to provide a consistent flow rate. For example, as shown, the position of the fluid conduits 720*a*, 720*b* may be different relative to each other. Specifically, a fluid input 722*a* of the first fluid conduit 720*a* may not be collinear with (e.g., offset from) a fluid input 722*b* of the second fluid conduit 720*b*. Similarly, a fluid output 724*a* of the first fluid conduit 720*a* may not be collinear with (e.g., offset from) a fluid output 724*b* of the second fluid conduit 720*b*. The rollers 712*a*, 712*b* may compress the fluid conduit 720*a* as the rotor 710*a* rotates in a direction indicated by the arrow in FIG. 7A. Similarly, The rollers 712*c*, 712*d* may compress the fluid conduit 720*b* as the rotor 710*b* rotates in a direction indicated by the arrow in FIG. 7B. Each fluid conduit 720*a*, 720*b* may comprise a first cross-sectional area in an uncompressed configuration and a second cross-sectional area in a compressed configuration, where the second cross-sectional area is less than the first cross-sectional area. In some variations, the second cross-sectional area may be zero, such that no liquid may flow past the compressed section. Due to the different positions of the respective fluid inputs 722*a*, 722*b* and fluid outputs 724*a*, 724*b* relative to each other, the fluid may enter and/or exit the respective fluid conduits 720*a*, 720*b* at different times. Accordingly, the fluid flowing through the respective fluid conduits 720*a*, 720*b* may be compressed at different times and thus any resulting pulses (e.g., periods of zero or near-zero liquid flow) may be mitigated. Put another way, a period of zero or near-zero liquid flow in the fluid flow through the fluid conduit 720*a* may be combined with a period of non-zero liquid flow in the fluid flow through the fluid conduit 720*b*, such that the overall liquid flow rate is non-zero.

As another example, FIG. 7B illustrates a second configuration of each of the first and second rotors 710*a*, 710*b*. In contrast to the first configuration of FIG. 7A in which the rollers of each respective rotor are collinear and the inlets and outlets of each respective fluid conduit are offset, in the second configuration shown in FIG. 7B the fluid inputs 722*a*, 722*b* and fluid outputs 724*a*, 724*b* of each respective fluid conduit may be collinear and the rollers of each respective rotor may be offset relative to each other. Accordingly, fluid may enter and exit each fluid conduit 720*a*, 720*b* at approximately the same time and position, but the rollers 712*a*, 712*b* of the first rotor 710*a* may compress the first fluid conduit 720*a* at a different time relative to the compression of the second fluid conduit 720*b* by the rollers 712*c*, 712*d* of the second rotor 710*b*. Accordingly, similar to the combined flow facilitated by the first configuration shown in FIG. 7A, the fluid flowing through the respective fluid conduits 720*a*, 720*b* may be compressed at different times and thus any resulting pulses (e.g., periods of zero or near-zero liquid flow) may be mitigated. Therefore, a period of zero or near-zero liquid flow in the fluid flow through the fluid conduit 720*a* may be combined with a period of non-zero liquid flow in the fluid flow through the fluid conduit 720*b*, such that the overall liquid flow rate may be non-zero.

Figure 8A:
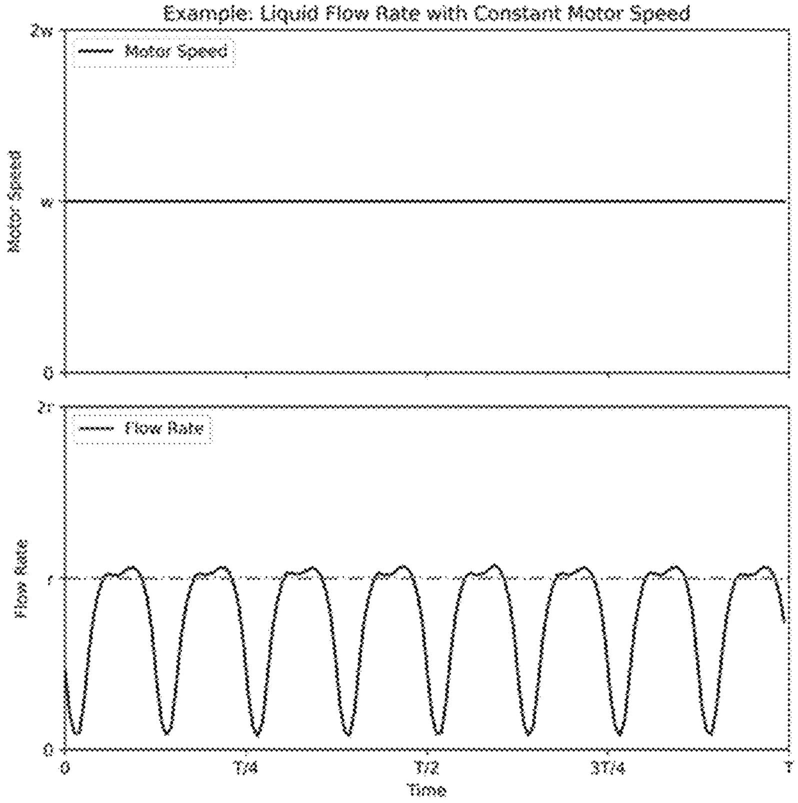
FIG. 8A is an illustrative variation of a plot of motor speed and flow rate over time with a single fluid conduit.
Figure 8B:
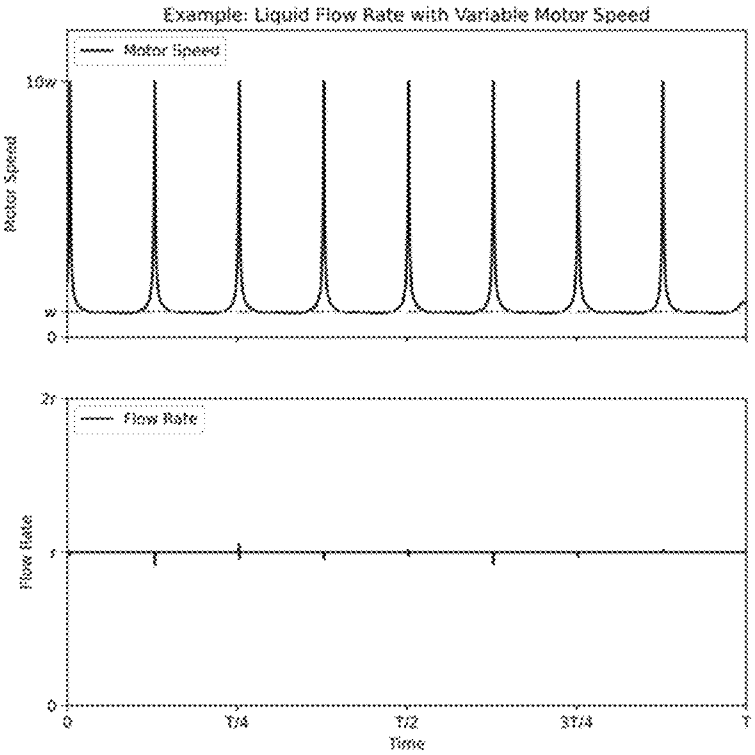
FIG. 8B is another illustrative variation of a plot of motor speed and flow rate over time with a single fluid conduit.

Additionally or alternatively, a liquid flow rate may be adjusted by modifying a rate of rotation of a rotor in either a closed loop or open loop manner. For example, FIGS. 8A and 8B illustrate flow rate data associated with a single fluid pathway operatively coupled to a single rotor with differing motor configurations. As shown, FIG. 8A illustrates flow rate data through a single fluid pathway (e.g., fluid conduit) while maintaining a rotor at a constant rate of rotation. The constant rate of rotation corresponds to a constant motor speed at a nominal motor speed value, w. Accordingly, the flow rate fluctuates between a near-zero value and a nominal flow rate value, r. The relative peaks and valleys indicate the pulses corresponding to compression of the fluid conduit by a roller coupled to the rotor. In contrast, FIG. 8B illustrates flow rate data through a single fluid pathway (e.g., fluid conduit) while varying the motor speed such that the rotor has a variable rate of rotation. As shown, the flow rate is maintained at the nominal flow rate value, r, while the motor speed fluctuates between the nominal motor speed value, w, and a second motor speed value, 10w. The nominal motor speed value, w, may be used during periods where the fluid conduit is in an uncompressed configuration whereas the second motor speed value, 10w, may be used during periods where the fluid conduit is in a compressed configuration. Accordingly, the data illustrates that varying the motor speed can effectively mitigate the effects of intermittent compression of the fluid conduit by one or more rollers coupled to the rotating rotor.

Figure 9A:
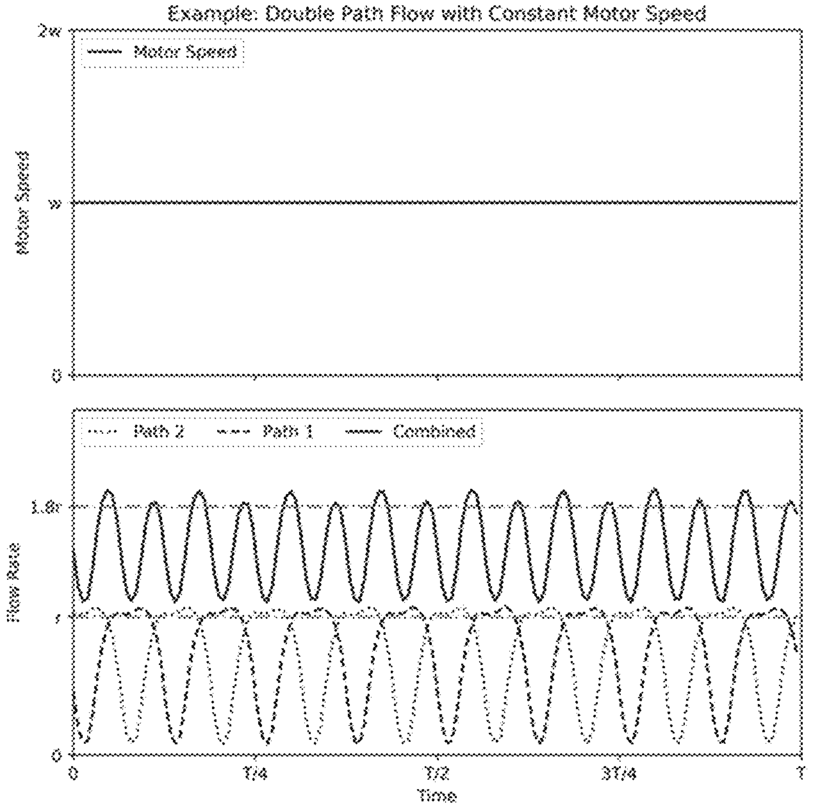
FIG. 9A is an illustrative variation of a plot of motor speed and flow rate over time with two fluid conduits.
Figure 9B:
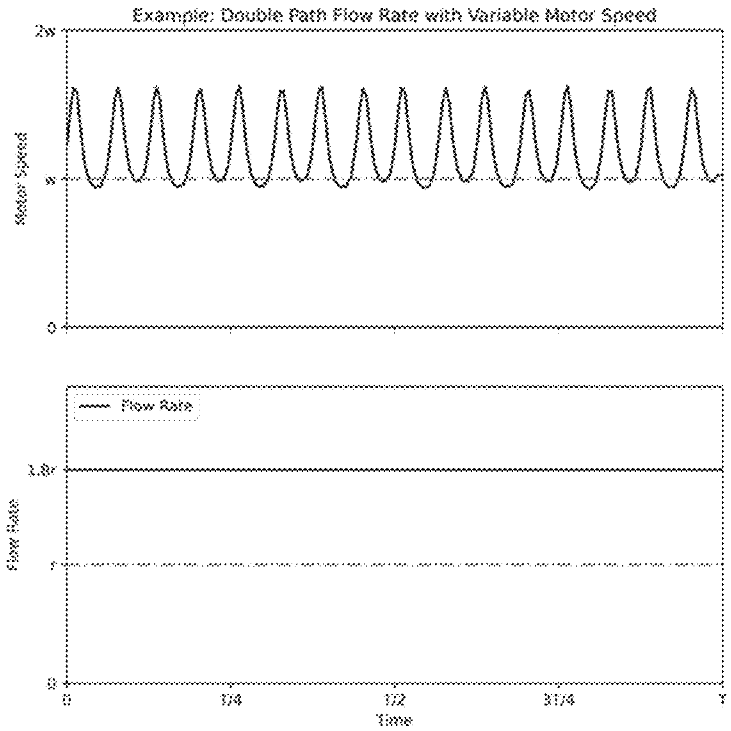
FIG. 9B is another illustrative variation of a plot of motor speed and flow rate over time with two fluid conduits.

The effects on flow rate facilitated by the first or second configurations shown in FIGS. 7A and 7B, respectively, may be enhanced when combined with the effects on flow rate facilitated by the variable motor speed shown in FIGS. 8A and 8B. For example, FIGS. 9A and 9B illustrate flow rate data associated with two fluid pathways with differing motor configurations. In particular, FIG. 9A illustrates flow rate data through each of a first flow path and a second flow path (e.g., first and second fluid conduits) that are operatively coupled to separate rotors in the configuration shown in FIG. 7A. Accordingly, the fluid flow from each of the first and second flow paths may be combined downstream of the respective rotors. As shown, the motor speed is maintained at the nominal motor speed value, w. In each of the first and second fluid conduits, the respective flow rates fluctuate between a near-zero value and a nominal flow rate value, r. The relative peaks and valleys indicate the pulses corresponding to compression of the fluid conduit by a roller coupled to the rotor. Additionally, the combined flow may correspond to a combined flow rate. As shown, the combined flow rate may fluctuate between the nominal flow rate value, r, and a second flow rate value, 1.8r. Accordingly, the combined flow rate may be non-zero but still exhibit some pulses that may be unsuitable for certain cell processing steps that require a specific, consistent flow rate value.

For cell processing steps that require specific, consistent flow rate values, the motor speed may be modified in combination with combining fluid from two fluid pathways. For example, FIG. 9B illustrates flow rate data through each of a first flow path and a second flow path (e.g., first and second fluid conduits) that are operatively coupled to separate rotors in the configuration shown in FIG. 7A. Accordingly, the fluid flow from each of the first and second flow paths may be combined downstream of the respective rotors. As shown, the motor speed alternates between the nominal motor speed, w, and a second motor speed value, 1.6w. The nominal motor speed value, w, may be used during periods where each of the fluid conduits is in an uncompressed configuration whereas the second motor speed value, 1.6w, may be used during periods where each of the fluid conduits is in a compressed configuration. The combined flow may correspond to a combined flow rate. As shown, the combined flow rate may consistently be the nominal flow rate value, r. Accordingly, the data illustrates that varying the motor speed in combination with multiple flow paths can effectively mitigate the effects of intermittent compression of each fluid conduit by one or more rollers coupled to one or more rotating rotors.

As described herein, a flow rate through one or more fluid conduits may be modified by adjusting a rate of rotation of a rotor in either a closed loop or open loop manner. The rate of rotation of the rotor may be controlled using a controller, such as the controller 178 described in reference to FIG. 1C. In some variations, the controller 178 may operate in a closed loop system or an open loop system. For example, in an open loop system, the flow rate may not be directly measured. Instead, one or more sensors may be configured to measure one or more parameters of the rotor and/or motor (e.g., a torque value, a rotor position value, a motor current value) and communicate the one or more measured parameters to the controller 178. The one or more measured parameters of the rotor and/or motor may be used to estimate a flow rate. For example, an empirical model may be used to compare the one or more measured parameters to previously collected data that was collected simultaneously with collecting flow rate data. Subsequently, the empirical model may be used to estimate a flow rate based on the one or more measured parameters. In turn, the controller 178 may modify the flow rate by, for example, modifying the rate of rotation of the rotor. In another example, in a closed loop system, one or more sensors may be configured to directly measure a flow rate through one or more fluid conduits and communicate the measured flow rate to the controller 178. Similar to the open loop system, the controller may modify the flow rate by, for example, modifying a rate of rotation of a rotor.

Figure 12A:
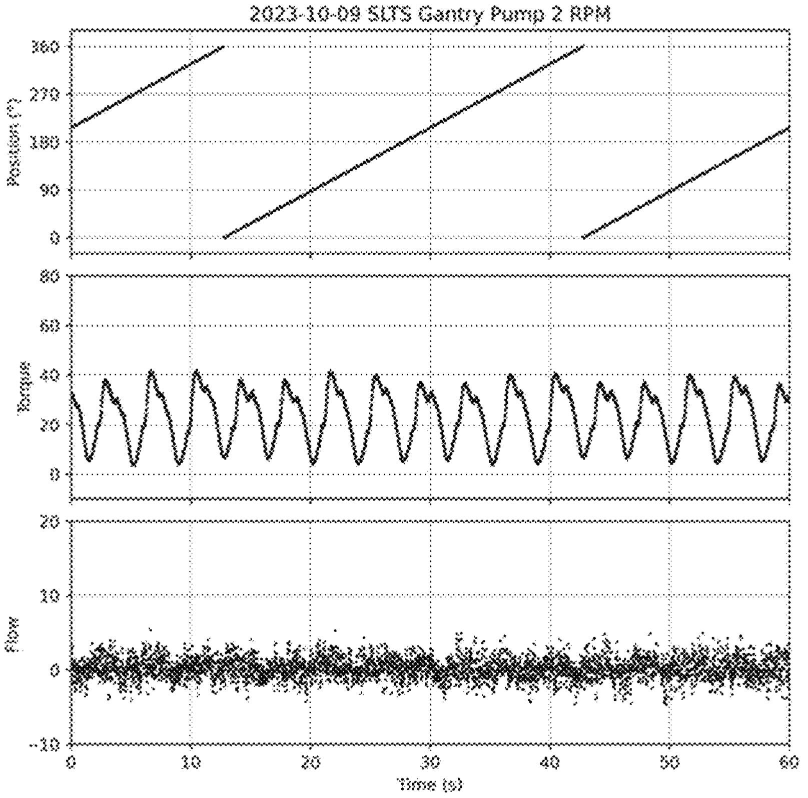
FIG. 12A is an illustrative variation of a plot of rotor position, torque, and flow rate over time.
Figure 12B:
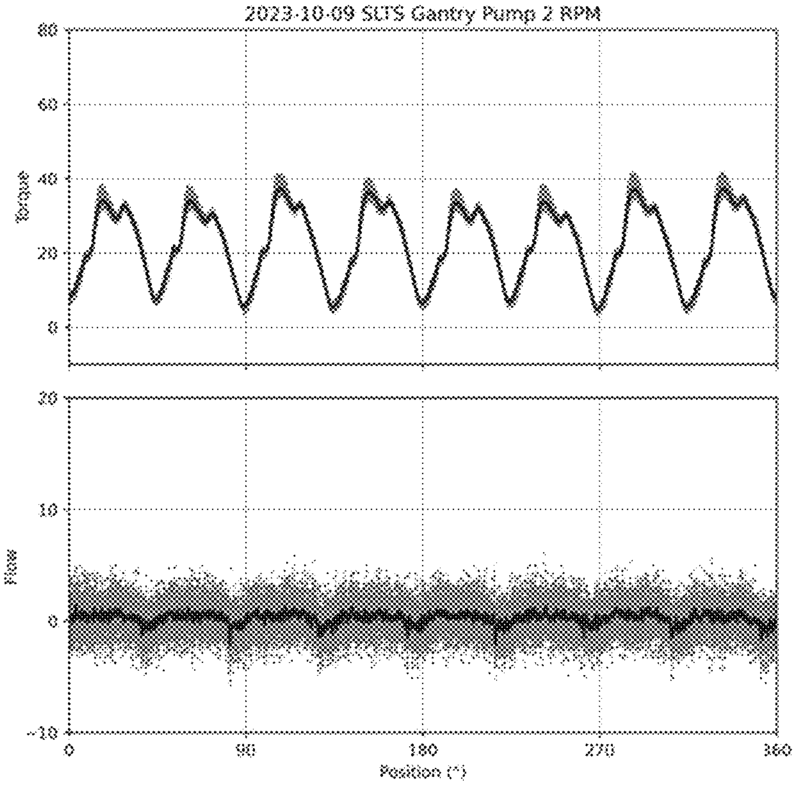
FIG. 12B is an illustrative variation of a plot of torque and flow rate over rotor position.

The use of an empirical model may be particularly advantageous in view of limitations associated with direct flow rate measurements, especially with small volumes of fluid (e.g., about 1 mL or less). For example, FIGS. 12A and 12B show data corresponding to a pump module with a rotating rotor that intermittently compresses a fluid conduit. As shown in FIG. 12A, a position of the rotor, a torque value of a motor coupled to the rotor, and a flow rate were each collected relative to time. The position data was collected by a position sensor operatively coupled to the rotor, the torque value was collected by a torque sensor operatively coupled to the motor, and the flow rate was collected by a flow rate sensor operatively coupled to the fluid conduit. The measured flow rate data is relatively noisy compared to the position and torque measurements. Accordingly, FIG. 12B illustrates the use of an empirical model to estimate a flow rate based on one or more of the torque and position measurements. In particular, a torque value and a flow rate value were each collected relative to rotor position. The measured flow rate values are provided in a light grey in FIG. 12B and indicate a relatively wide range of values. Subsequently, an empirical model was used to estimate a flow rate and plotted over the measured flow rate values in dark grey, which are generally smaller in magnitude and spread across a smaller range than the measured values. Accordingly, the estimated flow rates are significantly more precise than the measured flow rates due to the relatively large noise associated with flow rate sensors. Therefore, it may be particularly advantageous to utilize an empirical model, particularly in the case of small volumes of fluid (e.g., about 1 mL or less), because the model may be configured to more precisely estimate a flow rate and thus avoid inaccuracies associated with flow rate sensors.

Figure 10:
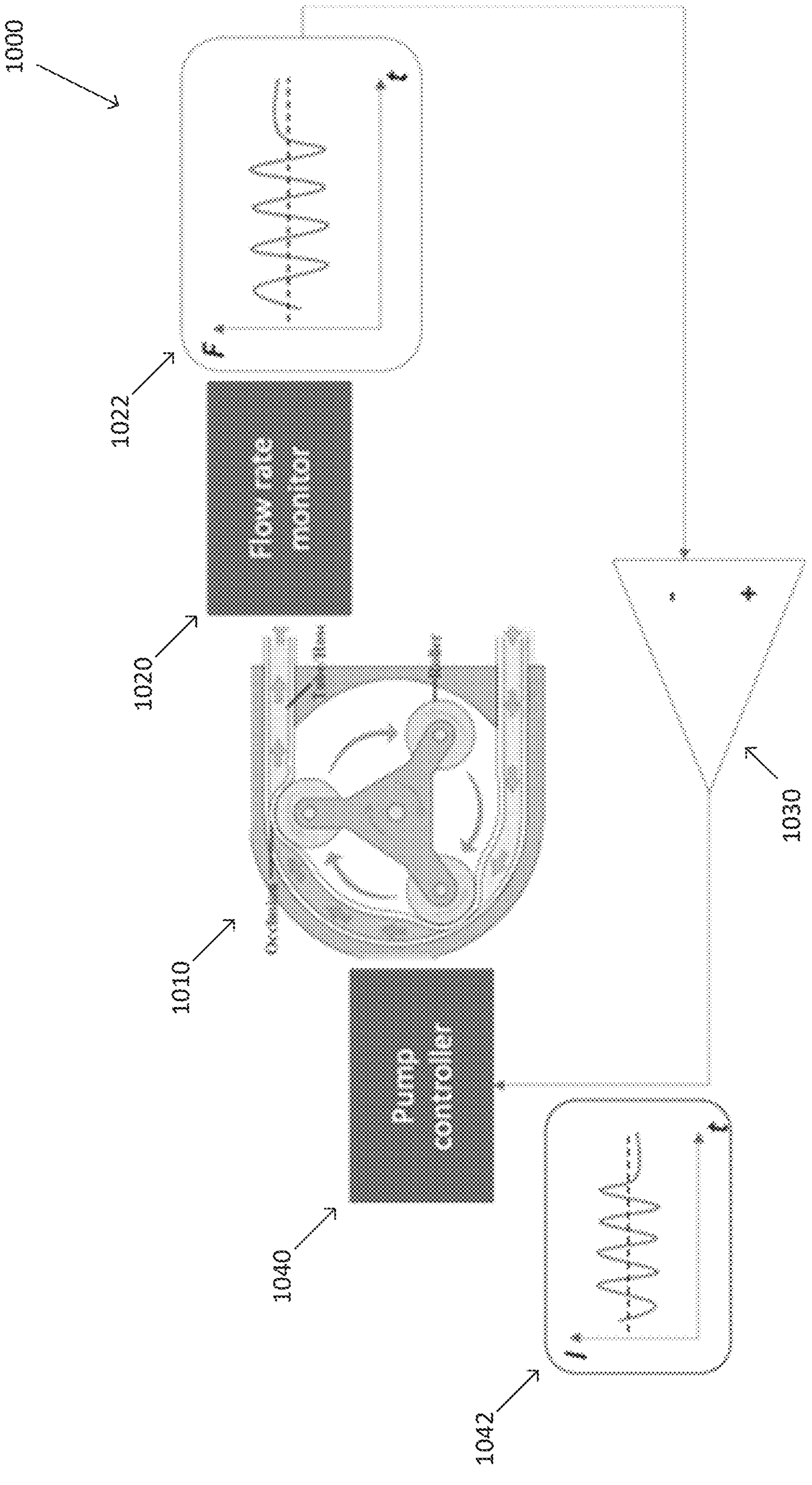
FIG. 10 is an illustrative schematic diagram of a pump module, a controller, and a flow rate monitor.

FIG. 10 illustrates an exemplary variation of a closed loop system 1000. The closed loop system 1000 may use a feedback loop from one or more sensors that communicate with a controller. For example, as shown, the closed loop system 1000 may comprise a pump module 1010, a flow rate monitor 1020, an electrical circuit 1030, and a pump controller 1040. The pump module 1010 may comprise a rotor comprising a plurality of rollers and a fluid conduit, such that the plurality of rollers may compress the fluid conduit to facilitate fluid flow. The flow rate monitor 1020 may be operatively coupled to the pump module 1010 in order to measure one or more parameters associated with the fluid flow through the pump module 1010. The one or more measured parameters may be displayed on a flow rate monitor display 1022 (e.g., a screen). For example, the flow rate monitor 1020 may be configured to measure a flow rate and/or a flow velocity at the inlet and/or outlet of the fluid conduit of the pump module 1010. The flow rate monitor 1020 may be electrically connected to the electrical circuit 1030. Additionally, the electrical circuit 1030 may be electrically connected to the pump controller 1040. The electrical circuit 1030 may be configured to modify an input to the pump controller 1040. For example, the electrical circuit may be configured to apply an inverse signal to the input to the pump controller 1040. In particular, in some variations, the inverse signal may correspond to a decrease in motor current to facilitate a decrease in a rate of rotation of the rotor. In further variations, the inverse signal may correspond to an increase in motor current to facilitate an increase in a rate of rotation of the rotor. One or more signals delivered to and/or provided by the pump controller may be displayed on a pump controller display 1042 (e.g., a screen).

The feedback loop used by the closed loop system 1000 may be configured to adjust the rate of rotation of the rotor in order to minimize variations (e.g., pulses) in the fluid flow. For example, the pulses of the flow may be periodic and thus predictable, which may be referred to as periodic error. Accordingly, the flow rate monitor 1020 may monitor (e.g., measure) the flow in and/or out of the pump module 1010 for one or more rotations of the rotor and, in some variations, may use the measurements to minimize pulses in future cycles by adjusting (e.g., increasing or decreasing) a rate of rotation of the rotor, which may be referred to as applying a periodic error correction. Each full rotation (e.g., about 360 degrees) of the rotor may correspond to one cycle that may include one or more pulses. The quantity of pulses per cycle may correspond to the quantity of rollers coupled to the rotor of the pump module 1010. For example, a single pulse in a cycle may correspond to a rotor comprising a single roller. In another example, 8 pulses in a cycle may correspond to a rotor comprising 8 rollers. In some variations, the flow rate monitor 1020 may measure between about 1 and about 100 cycles, about 1 and about 50 cycles, about 1 and about 40 cycles, about 1 and about 20 cycles, about 5 and about 20 cycles, or about 8 and about 12 cycles. In an exemplary variation, the flow rate monitor 1020 may measure less than 10 cycles. Subsequently, the measurements may be used to minimize pulses in subsequent cycles, which may or may not be actively monitored by the flow rate monitor 1020. For example, the measurements may be used by the electrical circuit 1030 and/or the pump controller 1040 to increase a rate of rotation of the rotor (e.g., by increasing a motor voltage and/or current) when a cross-sectional area of the fluid conduit is small (e.g., when the fluid conduit may be compressed by a roller) and/or decrease a rate of rotation of the rotor (e.g., by decreasing a motor voltage and/or current) when a cross-sectional area of the fluid conduit is large, which may reduce the quantity and/or magnitude of pulses in a subsequent cycle.

II. Methods of Pumping Fluid

Generally, the pump modules (e.g., fluid pumping devices, pump assemblies) described herein may pump fluid to and/or from one or more modules of a cell processing workcell. The pumping of fluid may be performed according to a pre-determined workflow. The workflow may be pre-programmed by a user via a controller of the workcell. In some variations, the pump modules may be controlled to deliver fluid to the one or more other modules of a cartridge according to any workflow. The pump modules may be fluidically connected to one or more fluid containers used to provide solutions or reagents, store cell products, or to collect waste solutions or reagents. The pump modules described herein may be coupled to a pump actuator of an instrument within a workcell to pump fluid, and the fluid may be pumped in a continuous or pulsatile manner. The pump modules may pump fluid by compressing a fluid conduit. For example, a pump module may comprise a peristaltic pump having a rotor with one or more rollers. The rotor may rotate such that the one or more rollers translate along a surface of the fluid conduit. As the one or more rollers translates along the surface of the fluid conduit, the fluid conduit may be compressed by the one or more rollers. Advantageously, the use of one or more rollers as described herein may maintain a sterile fluid flow path through the pump modules. In particular, the rollers may only engage an external surface of the fluid conduit, such that the fluid may not directly contact any component of the pump modules other than an internal surface of the fluid conduit.

The pump modules described herein may be configured to maintain a consistent flow rate of fluid pumped therethrough. For example, the pump modules may be controlled by a controller such that the rotor rotates at a predetermined rate of rotation which, in turn, may correspond to a flow rate for any given module. The flow rate may correspond to a cell processing step according to a predefined workflow. The fluid flowing at the predetermined flow rate may be transferred directly to the module configured to perform the cell processing step. In some variations, the fluid may flow indirectly to the module via, for example, the fluidic manifold.

Methods of pumping fluid may generally include providing fluid to a pump module and pumping the fluid at a flow rate through a fluid conduit of the pump module such that the fluid may be provided to one or more other modules of a cartridge. The flow rate may be modified according to the requirements of a given module in a closed loop or open loop manner. For example, a given module may require a relatively low flow rate that may be maintained at a consistent value. In other variations, a module may require a relatively high flow and may accommodate inconsistencies (e.g., pulses) in the flow rate. Accordingly, the flow rate may be modified by altering one or more parameters of the pump module. The modification of the flow rate may be performed in an open loop or closed loop system. For example, in an open loop system, one or more sensors may be configured to measure one or more parameters of the pump position and communicate the one or more measured parameters to a controller. In turn, the controller may modify the flow rate by, for example, modifying a rate of rotation of a rotor. In another example, in a closed loop system, one or more sensors may be configured to measure the flow rate and communicate the measured flow rate to a controller. Similar to the open loop system, the controller may modify the flow rate by, for example, modifying a rate of rotation of a rotor.

Figure 11:
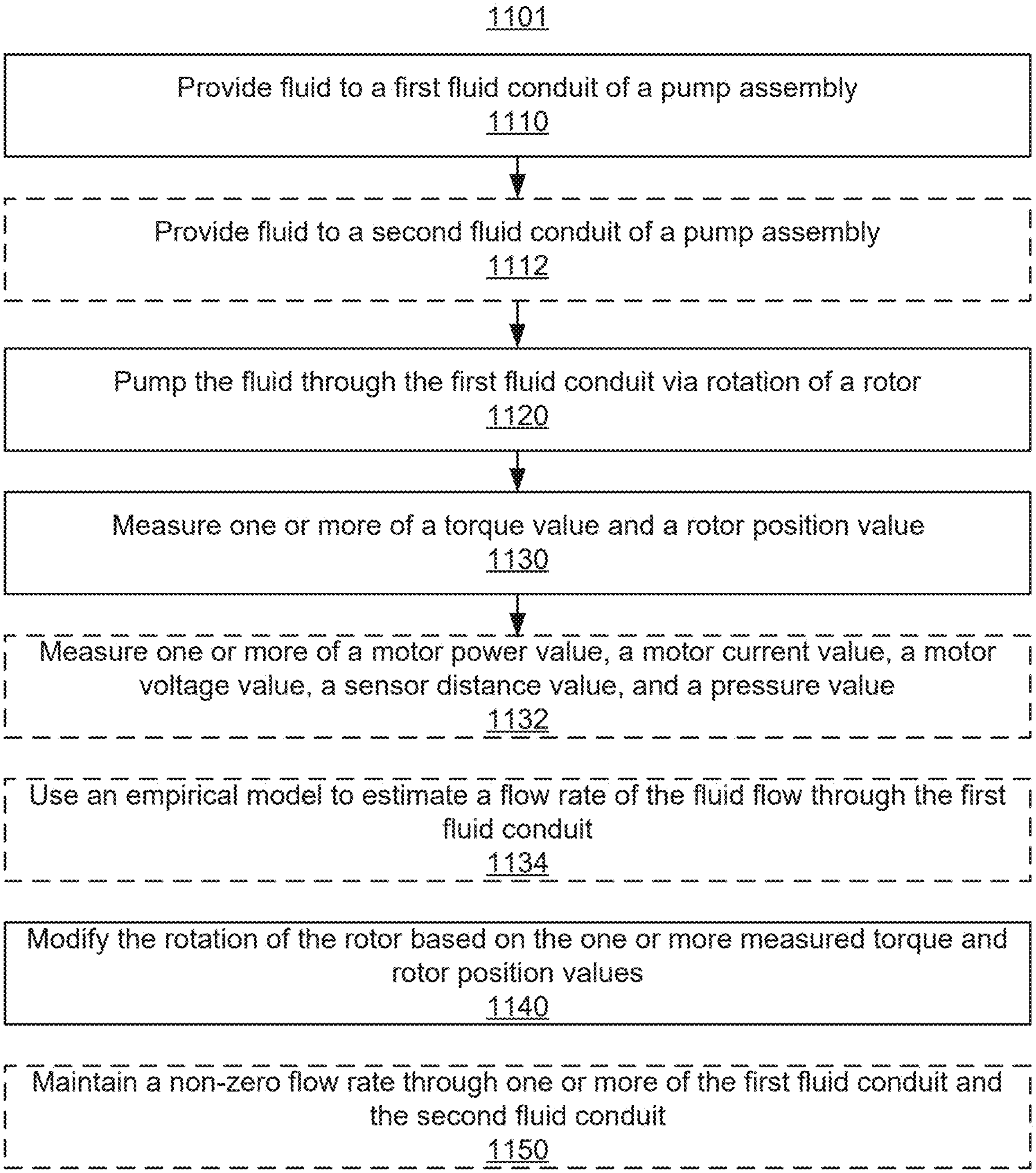
FIG. 11 is a flowchart of an illustrative variation of controlling fluid flow using a pump module of a cartridge comprising a fluid pumping device.

FIG. 11 provides a flowchart of an illustrative method of controlling fluid flow, for example, for use in cell processing. As shown, a method 1101 may include providing a fluid to a first fluid conduit of a pump assembly 1110. The fluid may comprise a liquid and/or a gas and may comprise one or more of cell culture media, buffer, cytokines, proteins, enzymes, polynucleotides, transfection reagents, non-viral vectors, viral vectors, antibiotics, nutrients, cryoprotectants, solvents, cellular materials, and pharmaceutically acceptable excipients. The pump assembly may be fluidically connected to a fluid source, such as a sterile liquid transfer device and/or one or more modules of the cartridge, such as a fluidic manifold. The pump assembly may comprise any suitable pump, such as one or more of a direct lift pump, displacement pump, gravity pump, reciprocating pump, rotary pump, and peristaltic pump. In an exemplary variation, the pump assembly may comprise a peristaltic pump comprising a roller assembly, a lever assembly, a controller, and, optionally, a sensor. As described herein, the roller assembly may comprise a rotor comprising a plurality of rollers. The lever assembly may comprise a body, a first lever arm coupled to the body at a first hinge, a second lever arm coupled to the first lever arm at a second hinge, and a spring coupled to the first lever arm. Operatively coupled to the second lever arm may be the first fluid conduit.

Optionally, in some variations, the method 1101 may further include providing a fluid to a second fluid conduit of a pump assembly 1112. The fluid may the same as the fluid provided to the first fluid conduit, but need not be. The second fluid conduit may be operatively coupled to the second lever arm of the pump assembly. In some variations, the second fluid conduit may be coupled to a different second lever arm of a different pump assembly.

The method 1101 may further include pumping the fluid through the first fluid conduit via rotation of the rotor 1120. For example, the rotor may rotate about an axle at a rate determined by the controller. In particular, the controller may be in communication with a motor that may be operatively coupled to the rotor. Rotation of the rotor may cause the plurality of rollers to translate along an external surface of the first fluid conduit. The first fluid conduit may be compressed by the one or more rollers as the one or more rollers translates along the surface of the first fluid conduit.

The compression creates a volume of low pressure (e.g., a vacuum) at the point of compression, such that fluid may move from a volume of higher pressure to the volume of low pressure. Accordingly, translating the compressive force along the fluid conduit may cause fluid to move through the first fluid conduit.

The method 1101 may further include measuring one or more of a torque value and a rotor position value 1130. For example, the torque value may be measured by a torque sensor operatively coupled to the motor and the rotor position value may be measured by a position sensor (e.g., accelerometer) operatively coupled to the rotor. The torque and/or rotor position values may be measured continuously or discontinuously. Optionally, in some variations, the method 1101 may further include measuring one or more of a motor current value, a sensor distance value, and a pressure value 1132. For example, the motor current value may be measured by a current sensor operatively coupled to the motor. The sensor distance value may be measured by a distance sensor (e.g., optical sensor) operatively coupled to the rotor. In some variations, the distance sensor may be positioned adjacent to the rotor such that the distance sensor may measure if the rotor becomes misaligned with a fluid conduit. The pressure value may be measured by a pressure sensor (e.g., pressure transducer, force gauge) operatively coupled to the first fluid conduit. For example, the pressure sensor may be configured to detect a quantity of fluid as the fluid flows past the pressure sensor, which may correlate to a position of the rotor based on the timing of one or more pulses in the fluid flow. In some variations, the one or more sensors described herein may not be directly coupled to the pump module and/or cartridge, which may reduce costs and/or minimize steps during manufacturing and assembly.

Optionally, in some variations, the method 1101 may further include using an empirical model to estimate a flow rate of the fluid flow through the first fluid conduit 1134. For example, an empirical model may be used to compare the one or more measured parameters to previously collected data that was collected simultaneously with collecting flow rate data. Subsequently, the empirical model may be used to estimate a flow rate based on the one or more measured parameters. The use of an empirical model may be particularly advantageous in view of limitations associated with direct flow rate measurements. For example, noise attributable to the flow rate sensor may be greater in magnitude than an actual flow rate, particularly when relatively low flow rates are required by a given module and/or cell processing step. Therefore, the empirical model may use relatively more accurate, less noisy data (e.g., torque values, position values) to estimate a flow rate relative to using measured flow rate data.

The method 1101 may further include modifying the rotation of the rotor based on the one or more measured torque and rotor position values 1140. For example, the rate of rotation of the rotor may be modified by the controller. That is, the controller may receive one or more of the measured torque and rotor position values and subsequently modify, or keep constant, an electrical signal communicated to the motor. In turn, the motor may modify, or keep constant, a rate of rotation of the rotor. The rate of rotation may be proportional to the flow rate through the first fluid conduit. In particular, a volumetric liquid flow rate may be proportional to a cross-sectional area of the fluid conduit and the rate of rotation of the rotor. Accordingly, in some variations, the rate of rotation of the rotor may be varied such that the flow rate may be maintained at a consistent value. That is, a decrease in the rate of rotation when the cross-sectional area is large and/or an increase in the rate of rotation when the cross-sectional area is small may yield a comparatively smoother flow rate.

Optionally, in some variations, the method 1101 may further include maintaining a non-zero flow rate through one or more of the first fluid conduit and the second fluid conduit 1150. For example, during operation of the pump assembly described herein each of the first and second fluid conduits may transition between an uncompressed configuration that may correspond to a first cross-sectional area and a compressed configuration that may correspond to a second cross-sectional area, where the second cross-sectional area is less than the first cross-sectional area. In some variations, the second cross-sectional area may be zero, such that no liquid may flow past the compressed section. Accordingly, flow through each of the first fluid conduit and the second fluid conduit may be combined downstream of the pump assembly such that any remaining variances (e.g., pulses) in the flow rate of either of the first or second fluid conduits may be mitigated. The non-zero flow rate may be further facilitated by offsetting one or more of a plurality of rollers coupled to one or more rotors configured to engage with the first and second fluid conduits and/or offsetting one or more of the fluid inlets and fluid outlets of the first and second fluid conduits. Put another way, altering the timing of compression of the first and second fluid conduits relative to each other may result in a non-zero flow rate when the liquid flow from the first and second fluid conduits may be combined.

Throughout this application, the term "about" is used to indicate that a value includes the inherent variation of error for the device or the method being employed to determine the value, or the variation that exists among the samples being measured. Unless otherwise stated or otherwise evident from the context, the term "about" means within 10% above or below the reported numerical value (except where such number would exceed 100% of a possible value or go below 0%). When used in conjunction with a range or series of values, the term "about" applies to the endpoints of the range or each of the values enumerated in the series, unless otherwise indicated. As used in this application, the terms "about" and "approximately" are used as equivalents.

While embodiments of the present invention have been shown and described herein, those skilled in the art will understand that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of controlling fluid flow comprising:

providing fluid to a first fluid conduit of a pump assembly, the pump assembly further comprising a lever arm and a rotor operatively coupled to a pump motor, wherein the rotor comprises one or more rollers configured to compress the first fluid conduit;

pumping the fluid through the first fluid conduit via rotation of the rotor at a rate of about 1 rpm to about 20 rpm;

measuring a torque value and a rotor position value, wherein the rotor position value defines a position of the one or more rollers relative to the first fluid conduit; and modifying the rotation of the rotor during a single revolution based on a flow rate estimated using at least the measured torque value and the rotor position value to modify fluid flow through the first fluid conduit and to maintain a consistent flow rate.

2. The method of claim 1 further comprising measuring one or more of a motor power value, a motor current value, a sensor distance value, and a pressure value.

3. The method of claim 1, wherein an empirical model is used to estimate the flow rate.

4. The method of claim 1, wherein modifying the rotation of the rotor is performed in a closed loop.

5. The method of claim 1, wherein modifying the rotation of the rotor is performed in an open loop.

6. The method of claim 1 further comprising providing the fluid to a second fluid conduit of the pump assembly.

7. The method of claim 6 further comprising maintaining a non-zero flow rate through one or more of the first fluid conduit and the second fluid conduit.

* * * * *